United States Patent
Crawford

(10) Patent No.: US 10,350,013 B2
(45) Date of Patent: Jul. 16, 2019

(54) SURGICAL TOOL SYSTEMS AND METHODS

(71) Applicant: GLOBUS MEDICAL, INC., Audubon, PA (US)

(72) Inventor: Neil R. Crawford, Chandler, AZ (US)

(73) Assignee: Globus Medical, Inc., Audubon, PA (US)

( * ) Notice: Subject to any disclaimer, the term of this patent is extended or adjusted under 35 U.S.C. 154(b) by 469 days.

(21) Appl. No.: 15/156,903

(22) Filed: May 17, 2016

(65) Prior Publication Data

US 2016/0331479 A1 Nov. 17, 2016

Related U.S. Application Data

(63) Continuation-in-part of application No. 14/062,707, filed on Oct. 24, 2013, which is a continuation-in-part
(Continued)

(51) Int. Cl.
*A61B 34/30* (2016.01)
*A61B 34/20* (2016.01)
(Continued)

(52) U.S. Cl.
CPC .............. *A61B 34/30* (2016.02); *A61B 5/062* (2013.01); *A61B 34/20* (2016.02); *A61B 90/96* (2016.02);
(Continued)

(58) Field of Classification Search
CPC ......... A61B 34/20; A61B 34/30; A61B 90/96; A61B 90/98
See application file for complete search history.

(56) References Cited

U.S. PATENT DOCUMENTS

| | | |
|---|---|---|
| 4,150,293 A | 4/1979 | Franke |
| 5,246,010 A | 9/1993 | Gazzara et al. |

(Continued)

FOREIGN PATENT DOCUMENTS

| | | |
|---|---|---|
| EP | 0744633 A2 | 11/1996 |
| EP | 2286729 A2 | 2/2011 |

(Continued)

OTHER PUBLICATIONS

Edward Ramsden, Hall Effect Sensors; Theory and Application (2nd Edition), pp. 107-130, http://store.elsevier.com/Hall-Effect-Sensors/Edward-Ramsden/isbn-9780080523743/. Feb. 28, 2006.
(Continued)

*Primary Examiner* — Tse W Chen
*Assistant Examiner* — Joanne M Hoffman

(57) ABSTRACT

Medical robot systems, surgical tool assemblies, devices, and methods regarding the same. The medical robot system may include a robot coupled to an end-effector having a guide tube. The robot may be configured for controlled movement and positioning of the end-effector. The system further includes a motor assembly coupled to the robot. The motor assembly may be configured to move the end-effector along one or more of an x-axis, a y-axis, and a z-axis. The surgical instrument is positionable and/or slidable within the guide tube. The surgical instrument includes at least one detectable feature, such as a reflective lens or stripe. A detection device is configured and arranged to detect the at least one detectable feature. The system enables a depth of the surgical instrument in the guide tube to be determined by the at least one detectable feature on the instrument.

8 Claims, 21 Drawing Sheets

Related U.S. Application Data of application No. 13/924,505, filed on Jun. 21, 2013, now Pat. No. 9,782,229.

(60) Provisional application No. 61/662,702, filed on Jun. 21, 2012, provisional application No. 61/800,527, filed on Mar. 15, 2013.

(51) Int. Cl.

| *A61B 5/06* | (2006.01) |
|---|---|
| *A61B 90/96* | (2016.01) |
| *A61B 90/98* | (2016.01) |
| *A61B 17/17* | (2006.01) |
| *A61B 17/00* | (2006.01) |
| *A61B 90/11* | (2016.01) |
| *A61B 90/00* | (2016.01) |

(52) U.S. Cl.
CPC .............. *A61B 90/98* (2016.02); *A61B 5/064* (2013.01); *A61B 17/17* (2013.01); *A61B 90/11* (2016.02); *A61B 2017/00876* (2013.01); *A61B 2034/2051* (2016.02); *A61B 2034/2055* (2016.02); *A61B 2034/2068* (2016.02); *A61B 2090/034* (2016.02); *A61B 2090/0811* (2016.02); *A61B 2090/3937* (2016.02); *A61B 2090/3945* (2016.02)

(56) References Cited

U.S. PATENT DOCUMENTS

| | | | |
|---|---|---|---|
| 5,576,830 | A * | 11/1996 | O'Brien .................. G02B 5/205 250/231.1 |
| 5,598,453 | A | 1/1997 | Baba et al. |
| 5,772,594 | A | 6/1998 | Barrick |
| 5,987,960 | A | 11/1999 | Messner et al. |
| 6,031,888 | A | 2/2000 | Ivan et al. |
| 6,032,761 | A * | 3/2000 | Coste ........................ B66B 1/50 187/294 |
| 6,144,875 | A | 11/2000 | Schweikard et al. |
| 6,203,196 | B1 | 3/2001 | Meyer et al. |
| 6,276,471 | B1 | 8/2001 | Kratzenberg et al. |
| 6,306,126 | B1 | 10/2001 | Montezuma |
| 6,314,311 | B1 | 11/2001 | Williams et al. |
| 6,320,929 | B1 | 11/2001 | Von Der Haar |
| 6,477,400 | B1 | 11/2002 | Barrick |
| 6,484,049 | B1 | 11/2002 | Seeley et al. |
| 6,487,267 | B1 | 11/2002 | Wolter |
| 6,490,475 | B1 | 12/2002 | Seeley et al. |
| 6,501,981 | B1 | 12/2002 | Schweikard et al. |
| 6,535,756 | B1 | 3/2003 | Simon et al. |
| 6,614,453 | B1 | 9/2003 | Suri et al. |
| 6,614,871 | B1 | 9/2003 | Kobiki et al. |
| 6,619,840 | B2 | 9/2003 | Rasche et al. |
| 6,666,579 | B2 | 12/2003 | Jensen |
| 6,757,068 | B2 | 6/2004 | Foxlin |
| 6,782,287 | B2 | 8/2004 | Grzeszczuk et al. |
| 6,856,826 | B2 | 2/2005 | Seeley et al. |
| 6,856,827 | B2 | 2/2005 | Seeley et al. |
| 6,920,347 | B2 | 7/2005 | Simon et al. |
| 6,922,632 | B2 | 7/2005 | Foxlin |
| 6,988,009 | B2 | 1/2006 | Grimm et al. |
| 6,996,487 | B2 | 2/2006 | Jutras et al. |
| 7,016,457 | B1 | 3/2006 | Senzig et al. |
| 7,043,961 | B2 | 5/2006 | Pandey et al. |
| 7,062,006 | B1 | 6/2006 | Pelc et al. |
| 7,063,705 | B2 | 6/2006 | Young et al. |
| 7,072,707 | B2 | 7/2006 | Galloway, Jr. et al. |
| 7,099,428 | B2 | 8/2006 | Clinthorne et al. |
| 7,108,421 | B2 | 9/2006 | Gregerson et al. |
| 7,130,676 | B2 | 10/2006 | Barrick |
| 7,139,418 | B2 | 11/2006 | Abovitz et al. |
| 7,194,120 | B2 | 3/2007 | Wicker et al. |
| 7,197,107 | B2 | 3/2007 | Arai et al. |
| 7,231,014 | B2 | 6/2007 | Levy |
| 7,231,063 | B2 | 6/2007 | Naimark et al. |
| 7,301,648 | B2 | 11/2007 | Foxlin |
| 7,313,430 | B2 | 12/2007 | Urquhart et al. |
| 7,318,805 | B2 | 1/2008 | Schweikard et al. |
| 7,324,623 | B2 | 1/2008 | Heuscher et al. |
| 7,327,865 | B2 | 2/2008 | Fu et al. |
| 7,460,637 | B2 | 12/2008 | Clinthorne et al. |
| 7,493,153 | B2 | 2/2009 | Ahmed et al. |
| 7,505,617 | B2 | 3/2009 | Fu et al. |
| 7,623,902 | B2 | 11/2009 | Pacheco |
| 7,643,862 | B2 * | 1/2010 | Schoenefeld .......... A61B 90/36 600/407 |
| 7,661,881 | B2 | 2/2010 | Gregerson et al. |
| 7,683,331 | B2 | 3/2010 | Chang |
| 7,683,332 | B2 | 3/2010 | Chang |
| 7,702,379 | B2 | 4/2010 | Avinash et al. |
| 7,702,477 | B2 | 4/2010 | Tuemmler et al. |
| 7,711,083 | B2 | 5/2010 | Heigl et al. |
| 7,725,253 | B2 | 5/2010 | Foxlin |
| 7,726,171 | B2 | 6/2010 | Langlotz et al. |
| 7,760,849 | B2 | 7/2010 | Zhang |
| 7,796,728 | B2 | 9/2010 | Bergfjord |
| 7,813,838 | B2 | 10/2010 | Sommer |
| 7,835,778 | B2 | 11/2010 | Foley et al. |
| 7,835,784 | B2 | 11/2010 | Mire et al. |
| 7,840,256 | B2 | 11/2010 | Lakin et al. |
| 7,844,320 | B2 | 11/2010 | Shahidi |
| 7,853,305 | B2 | 12/2010 | Simon et al. |
| 7,853,313 | B2 | 12/2010 | Thompson |
| 7,900,524 | B2 | 3/2011 | Calloway et al. |
| 7,940,999 | B2 | 5/2011 | Liao et al. |
| 7,945,012 | B2 | 5/2011 | Ye et al. |
| 7,945,021 | B2 | 5/2011 | Shapiro et al. |
| 8,019,045 | B2 | 9/2011 | Kato |
| 8,021,310 | B2 | 9/2011 | Sanborn et al. |
| 8,052,688 | B2 | 11/2011 | Wolf, II |
| 8,086,299 | B2 | 12/2011 | Adler et al. |
| 8,098,914 | B2 | 1/2012 | Liao et al. |
| 8,100,950 | B2 | 1/2012 | St. Clair et al. |
| 8,116,430 | B1 | 2/2012 | Shapiro et al. |
| 8,121,249 | B2 | 2/2012 | Wang et al. |
| 8,150,494 | B2 | 4/2012 | Simon et al. |
| 8,208,708 | B2 | 6/2012 | Homan et al. |
| 8,224,024 | B2 | 7/2012 | Foxlin et al. |
| 8,311,611 | B2 | 11/2012 | Csavoy et al. |
| 8,335,557 | B2 | 12/2012 | Maschke |
| 8,358,818 | B2 | 1/2013 | Miga et al. |
| 8,379,791 | B2 | 2/2013 | Forthmann et al. |
| 8,386,019 | B2 | 2/2013 | Camus et al. |
| 8,394,099 | B2 | 3/2013 | Patwardhan |
| 8,462,911 | B2 | 6/2013 | Vesel et al. |
| 8,526,700 | B2 | 9/2013 | Isaacs |
| 8,541,970 | B2 | 9/2013 | Nowlin et al. |
| 8,560,118 | B2 | 10/2013 | Green et al. |
| 8,571,637 | B2 * | 10/2013 | Sheffer .................. A61B 34/20 128/845 |
| 8,597,198 | B2 | 12/2013 | Sanborn et al. |
| 8,611,985 | B2 | 12/2013 | Lavallee et al. |
| 8,630,389 | B2 | 1/2014 | Kato |
| 8,634,897 | B2 | 1/2014 | Simon et al. |
| 8,660,635 | B2 | 2/2014 | Simon et al. |
| 8,678,647 | B2 | 3/2014 | Gregerson et al. |
| 8,696,458 | B2 | 4/2014 | Foxlin et al. |
| 8,706,185 | B2 | 4/2014 | Foley et al. |
| 8,727,618 | B2 | 5/2014 | Maschke et al. |
| 8,738,115 | B2 | 5/2014 | Amberg et al. |
| 8,740,882 | B2 | 6/2014 | Jun et al. |
| 8,781,186 | B2 | 7/2014 | Clements et al. |
| 8,781,630 | B2 | 7/2014 | Banks et al. |
| 8,787,520 | B2 | 7/2014 | Baba |
| 8,792,704 | B2 | 7/2014 | Isaacs |
| 8,798,231 | B2 | 8/2014 | Notohara et al. |
| 8,812,077 | B2 | 8/2014 | Dempsey |
| 8,814,793 | B2 | 8/2014 | Brabrand |
| 8,818,105 | B2 | 8/2014 | Myronenko et al. |
| 8,821,511 | B2 | 9/2014 | Von Jako et al. |
| 8,867,703 | B2 | 10/2014 | Shapiro et al. |
| 8,888,821 | B2 | 11/2014 | Rezach et al. |

(56) References Cited

U.S. PATENT DOCUMENTS

| | | |
|---|---|---|
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,078,685 B2 * | 7/2015 | Smith ................ A61B 5/06 |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0196994 A1 * | 12/2002 | Bosselmann .......... G01B 11/14 |
| | | 385/12 |
| 2003/0055049 A1 | 3/2003 | Brock |
| 2004/0076259 A1 | 4/2004 | Jensen et al. |
| 2004/0152972 A1 * | 8/2004 | Hunter ............... A61B 17/025 |
| | | 600/424 |
| 2006/0142657 A1 * | 6/2006 | Quaid ................ G06F 19/00 |
| | | 600/424 |
| 2006/0161051 A1 * | 7/2006 | Terrill-Grisoni ....... A61B 90/36 |
| | | 600/300 |
| 2006/0172877 A1 * | 8/2006 | Fechner .............. A01N 59/16 |
| | | 501/48 |
| 2006/0184396 A1 | 8/2006 | Dennis et al. |
| 2006/0209019 A1 * | 9/2006 | Hu ..................... G06F 3/016 |
| | | 345/156 |
| 2006/0258938 A1 * | 11/2006 | Hoffman ........... A61B 1/00193 |
| | | 600/424 |
| 2006/0291612 A1 | 12/2006 | Nishide et al. |
| 2007/0038059 A1 | 2/2007 | Sheffer et al. |
| 2007/0073133 A1 | 3/2007 | Schoenefeld |
| 2008/0004523 A1 | 1/2008 | Jensen |
| 2008/0010706 A1 * | 1/2008 | Moses ............... A61B 17/1764 |
| | | 600/407 |
| 2008/0013809 A1 | 1/2008 | Zhu et al. |
| 2008/0082109 A1 | 4/2008 | Moll et al. |
| 2008/0108991 A1 | 5/2008 | Von Jako |
| 2008/0144906 A1 | 6/2008 | Allred et al. |
| 2008/0146942 A1 * | 6/2008 | Dala-Krishna .......... A61B 6/12 |
| | | 600/466 |
| 2008/0161680 A1 | 7/2008 | Von Jako et al. |
| 2008/0208006 A1 * | 8/2008 | Farr .................. A61B 1/0607 |
| | | 600/178 |
| 2008/0235052 A1 | 9/2008 | Node-Langlois et al. |
| 2008/0269596 A1 | 10/2008 | Revie et al. |
| 2008/0287781 A1 | 11/2008 | Revie et al. |
| 2008/0300477 A1 | 12/2008 | Lloyd et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0024142 A1 * | 1/2009 | Ruiz Morales .......... B25J 9/041 |
| | | 606/130 |
| 2009/0099445 A1 * | 4/2009 | Burger ............... A61B 90/36 |
| | | 600/424 |
| 2009/0185655 A1 | 7/2009 | Koken et al. |
| 2009/0198121 A1 | 8/2009 | Hoheisel |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130966 A1 * | 5/2010 | Brownell ............ A61B 3/1005 |
| | | 606/4 |
| 2010/0228117 A1 | 9/2010 | Hartmann |
| 2010/0274120 A1 | 10/2010 | Heuscher |
| 2011/0098553 A1 | 4/2011 | Robbins et al. |
| 2011/0257653 A1 * | 10/2011 | Hughes ................ A61B 34/10 |
| | | 606/79 |
| 2011/0282189 A1 | 11/2011 | Graumann |
| 2011/0286573 A1 | 11/2011 | Schretter et al. |
| 2011/0295240 A1 * | 12/2011 | Hamel ............ A61M 25/0017 |
| | | 604/544 |
| 2012/0029279 A1 * | 2/2012 | Kucklick ............ A61B 1/015 |
| | | 600/109 |
| 2012/0029280 A1 * | 2/2012 | Kucklick ............ A61B 1/015 |
| | | 600/109 |
| 2012/0035507 A1 | 2/2012 | George et al. |
| 2012/0051498 A1 | 3/2012 | Koishi |
| 2012/0053427 A1 * | 3/2012 | Markle ............ A61B 5/14532 |
| | | 600/301 |
| 2012/0143084 A1 | 6/2012 | Shoham |
| 2012/0226145 A1 | 9/2012 | Chang et al. |
| 2012/0235909 A1 | 9/2012 | Birkenbach et al. |
| 2012/0294498 A1 | 11/2012 | Popovic |
| 2013/0016889 A1 | 1/2013 | Myronenko et al. |
| 2013/0060146 A1 | 3/2013 | Yang et al. |
| 2013/0094742 A1 | 4/2013 | Feilkas |
| 2013/0113791 A1 | 5/2013 | Isaacs et al. |
| 2013/0165937 A1 | 6/2013 | Patwardhan |
| 2013/0281821 A1 | 10/2013 | Liu et al. |
| 2013/0307955 A1 | 11/2013 | Deitz et al. |
| 2013/0342578 A1 | 12/2013 | Isaacs |
| 2013/0345718 A1 | 12/2013 | Crawford et al. |
| 2013/0345757 A1 | 12/2013 | Stad |
| 2014/0046132 A1 | 2/2014 | Hoeg et al. |
| 2014/0049629 A1 | 2/2014 | Siewerdsen et al. |
| 2014/0066944 A1 | 3/2014 | Taylor et al. |
| 2014/0080086 A1 | 3/2014 | Chen |
| 2014/0096369 A1 | 4/2014 | Matsumoto et al. |
| 2014/0121676 A1 | 5/2014 | Kostrzewski et al. |
| 2014/0135796 A1 | 5/2014 | Simon et al. |
| 2014/0130810 A1 | 8/2014 | Azizian et al. |
| 2014/0221819 A1 | 8/2014 | Sarment |
| 2014/0234804 A1 | 8/2014 | Huang et al. |
| 2014/0275955 A1 * | 9/2014 | Crawford ............ A61B 5/062 |
| | | 600/409 |
| 2014/0371577 A1 | 12/2014 | Maillet et al. |
| 2014/0379130 A1 | 12/2014 | Lee et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0000514 A1 * | 1/2016 | Ellman ............ A61B 18/1442 |
| | | 606/1 |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0071691 A1 * | 3/2017 | Crawford ............ A61B 90/96 |
| 2017/0135770 A1 | 5/2017 | Scholl et al. |
| 2017/0140671 A1 * | 5/2017 | Chui ................... G09B 9/00 |
| 2017/0143284 A1 | 5/2017 | Sehnert et al. |
| 2017/0143426 A1 | 5/2017 | Isaacs et al. |
| 2017/0156805 A1 * | 6/2017 | Taylor ................ B25J 15/0466 |
| 2017/0156816 A1 | 6/2017 | Ibrahim |
| 2017/0202629 A1 | 7/2017 | Maillet et al. |
| 2017/0212723 A1 | 7/2017 | Atarot et al. |

(56) References Cited

U.S. PATENT DOCUMENTS

| | | |
|---|---|---|
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |

FOREIGN PATENT DOCUMENTS

| | | |
|---|---|---|
| JP | 898843 A | 4/1996 |
| JP | 8313304 A | 11/1996 |
| WO | 02071369 A1 | 9/2002 |
| WO | 2012018816 A3 | 2/2012 |

OTHER PUBLICATIONS

Shuanghi, Hao et al., Study on a novel absolute magnetic encoder, Robotice and Biomemetics, 2009, ROBIO, 2009. IEEE, International Conference on IEEE. pp. 1773-1776, Feb. 22, 2009.

Eric M. Yeatmann et al., "Use of Scanned Detection in Optical Position Encoders", IEEE, Transactions of Instrumentation and Measurement. vol. 53, No. 1, pp. 37-44. http://www3.imperial.ac.uk/pls/portallive/docs/1/375913.PDF. Feb. 28, 2004.

\* cited by examiner

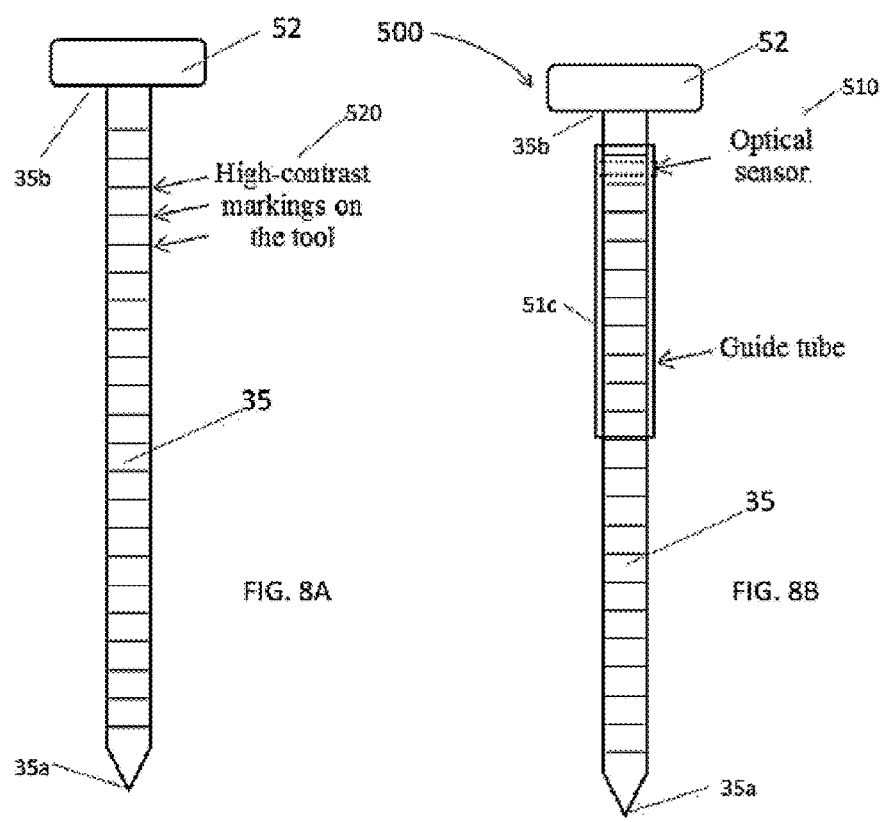

SURGICAL TOOL SYSTEMS AND METHODS

CROSS REFERENCE TO RELATED APPLICATIONS

This application is a continuation-in-part of U.S. patent application Ser. No. 14/062,707 filed Oct. 24, 2013, which is a continuation-in-part of U.S. patent application Ser. No. 13/924,505 filed on Jun. 21, 2013, which claims the priority to U.S. Provisional Patent App. No. 61/662,702 filed on Jun. 21, 2012 and U.S. Provisional Patent App. No. 61/800,527 filed on Mar. 15, 2013, all of which are incorporated by reference herein in their entireties for all purposes.

BACKGROUND

Various medical procedures require the accurate localization of a three-dimensional position of a surgical instrument within the body in order to effect optimized treatment. For example, some surgical procedures to fuse vertebrae require that a surgeon drill multiple holes into the bone structure at specific locations. To achieve high levels of mechanical integrity in the fusing system, and to balance the forces created in the bone structure, it is necessary that the holes are drilled at the correct location. Vertebrae, like most bone structures, have complex shapes including non-planar curved surfaces making accurate and perpendicular drilling difficult. Conventionally, a surgeon manually holds and positions a drill guide tube by using a guidance system to overlay the drill tube's position onto a three dimensional image of the bone structure. This manual process is both tedious and time consuming. The success of the surgery is largely dependent upon the dexterity of the surgeon who performs it.

Limited robotic assistance for surgical procedures is currently available. For example, the da Vinci® medical robot system (da Vinci® is a registered trademark of Intuitive Surgical) is a robot used in certain surgical applications. In the da Vinci® system, the user controls manipulators that control a robotic actuator. The system converts the surgeon's gross movements into micro-movements of the robotic actuator. Although the da Vinci® system eliminates hand tremor and provides the user with the ability to work through a small opening, like many of the robots commercially available today, it is expensive, obtrusive, and the setup is cumbersome. Further, for procedures such as thoracolumbar pedicle screw insertion, these conventional methods are known to be error-prone and tedious.

One of the characteristics of many of the current robots used in surgical applications which make them error prone is that autonomous movement and precise placement of a surgical instrument can be hindered by lack of mechanical feedback and/or loss of visual placement once the instrument is submerged within a portion of a patient.

SUMMARY

Some embodiments of the invention provide a guided surgical tool assembly comprising a guide tube including at least one sensor and a surgical instrument including at least one detectable feature moveable within the guide tube. In some embodiments, the at least one sensor is configured and arranged to detect the at least one detectable feature when the surgical instrument is at least partially inserted in the guide tube.

Some embodiments include a detectable feature comprising a magnetically detectable feature capable of generating a magnetic flux field, and in some embodiments, the sensor is a position sensor capable of detecting the magnetic flux field. Some embodiments also include a position sensor configured and arranged to detect insertion into and movement of the surgical instrument in the guide tube by sensing the magnetically detectable feature. In some embodiments, the position sensor is a magnetic flux field sensor selected from a group consisting of a ferrite-based magnetic material, a rare-earth based magnetic material, an aluminum-nickel-cobalt based magnetic material, and mixtures thereof.

In some embodiments, the detectable feature includes at least one longitudinal magnetic strip and at least one radial magnetic strip. Further, in some embodiments, the guide tube includes at least three position sensors, and in some embodiments, the at least three position sensors are configured and arranged to sense a magnetic field flux from the longitudinal magnetic strip or the radial magnetic field strip or both.

In some embodiments, the longitudinal position of the surgical instrument in the guide tube can be at least partially determined using a measurement of a magnetic field flux from the longitudinal magnetic strip. In other embodiments, a radial position of the surgical instrument in the guide tube can be at least partially determined using a measurement of a magnetic field flux from the radial magnetic strip.

Some embodiments include a detectable feature comprising an optically detectable feature, and at least one sensor comprising at least one optical sensor. In some embodiments, the optically detectable feature comprises a contrasting or high contrast marking distributed along at least a partial longitudinal length of the guided surgical tool assembly.

Some embodiments include at least one optical sensor comprising a light sensitive detector selected from a group consisting of a photodiode, a phototransistor, a fiber-optic sensor, a photo-multiplier, a CCD, a camera, or a combination thereof.

In some embodiments, the longitudinal position of the surgical instrument in the guide tube can be at least partially determined by optically sensing light from the high contrast marking using the at least one optical sensor.

Some embodiments include an optically detectable feature comprising a graduated coating distributed along at least a partial longitudinal length of the guided surgical tool assembly. In some embodiments, the graduated coating comprises a graduated reflective coating. In other embodiments, the graduated coating comprises a graduated color coating.

In some embodiments, the longitudinal position of the surgical instrument in the guide tube can be at least partially determined by optically sensing light from the graduated coating using the at least one optical sensor.

Some embodiments include a guided surgical tool assembly wherein the guide tube comprises a distal guide tube end and a proximal guide tube end, and the surgical instrument includes a distal end and a proximal end. In some embodiments, the sensor comprises at least one sensor pad. The guided surgical tool assembly can further comprise a guide stop coupled to the proximal end of the surgical instrument, and a plunger mechanism. The plunger mechanism can include a compressible spring mechanism coupled to the distal end of the guide tube and a wiper configured and arranged to be sensed by the at least one sensor pad.

In some embodiments of the guided surgical tool assembly, longitudinal movement of the surgical instrument within the guide tube (where the guide stop moves toward the proximal end of the guide tube) can at least partially compress the spring and move the wiper with respect to the at least one sensor pad. In other embodiments, longitudinal movement of the surgical instrument within the guide tube where the guide stop moves away from the proximal end of the guide tube can at least partially decompress the spring and move the wiper with respect to the at least one sensor pad.

Some embodiments include a guided surgical tool assembly system comprising a tool sensor system including at least one processor and at least one data input/output interface. In some embodiments, the data input interface including at least one sensor, a guide tube including the at least one sensor, and a surgical instrument moveable within the guide tube. In some embodiments, the surgical instrument includes at least one detectable feature, and the at least one sensor is configured and arranged to detect the at least one detectable feature.

In some embodiments, the guided surgical tool assembly system includes a guide tube comprising a distal guide tube end and a proximal guide tube end, and the surgical instrument includes a distal end and a proximal end. In some embodiments, the sensor comprises at least one sensor pad, and the guided surgical tool assembly further comprises a guide stop coupled to the proximal end of the surgical instrument, the plunger mechanism can include a compressible spring mechanism coupled to the distal end of the guide tube and a wiper configured and arranged to be sensed by the at least one sensor pad. The at least one processor can be configured and arranged to detect the at least one surgical instrument when the instrument at least partially inserted or moved in the guide tube.

In some embodiments of the guided surgical tool assembly system, the detectable feature comprises a magnetically detectable feature capable of generating a magnetic flux field. The sensor can be a position sensor capable of detecting the magnetic flux field, and be configured and arranged to detect insertion into and movement of the surgical instrument in the guide tube by sensing the magnetically detectable feature.

Some embodiments include a guided surgical tool assembly system in which the detectable feature comprises an optically detectable feature, and the at least one sensor comprises at least one optical sensor. The optically detectable feature can comprise a contrasting or high contrast marking distributed along at least a partial longitudinal length of the guided surgical tool assembly. In some embodiments, the detectable feature comprises an optically detectable feature, and the at least one sensor comprises at least one optical sensor. The optically detectable feature can comprise a graduated coating distributed along at least a partial longitudinal length of the guided surgical tool assembly.

Some embodiments include a medical robot system comprising a robot coupled to an effectuator element configured for controlled movement and positioning, and a motor assembly coupled to the robot. The motor assembly can be configured to move the effectuator element along one or more of an x-axis, a y-axis, and a z-axis such that movement of the effectuator element along one of the x-, y-, or z-axes occurs independently of movement of the effectuator element along the other axes of the x-, y-, and z-axes, wherein the x-axis is substantially perpendicular to the y- and z-axes, the y-axis is substantially perpendicular to the x- and z-axes, and the z-axis is substantially perpendicular to the x- and y axes.

In some embodiments, the medical robot system also comprises a tool sensor system including at least one processor and at least one data input/output interface, the data input interface including at least one sensor, and a guide tube including the at least one sensor. In some embodiments, the surgical instrument is moveable within the guide tube, and the surgical instrument includes at least one detectable feature. Further, in some embodiments, the at least one sensor is configured and arranged to detect the at least one detectable feature, and the at least one processor is configured and arranged to detect when the surgical instrument is at least partially inserted in the guide tube. In some embodiments, the detectable feature can include one or more of instrument length, type, torque ranges, depth of treatment parameters and other instrument parameters. Some embodiments include a tracking marker coupled to the surgical instrument.

Some embodiments include a guided surgical tool assembly comprising an end-effector including a guide tube; and a surgical instrument having a shaft and a handle, the surgical instrument moveable within the guide tube, the surgical instrument including at least one detectable feature affixed to the shaft or the handle, wherein a depth of the surgical instrument in the guide tube is determined by the at least one detectable feature.

In some embodiments, a medical robot system includes a robot coupled to an end-effector, the robot configured for controlled movement and positioning of the end-effector, the end-effector including a guide tube; a motor assembly coupled to the robot, the motor assembly being configured to move the end-effector along one or more of an x-axis, a y-axis, and a z-axis; a surgical instrument positionable within the guide tube, the surgical instrument including at least one detectable feature; and a detection device configured and arranged to detect the at least one detectable feature, wherein a depth of the surgical instrument in the guide tube is determined by the at least one detectable feature.

In one embodiment, the detectable feature may include a reflective lens or lenses, for example. For example, three reflective lenses may be arranged around an outer perimeter of the shaft of the surgical instrument. The reflective lens may be embedded in the handle of the surgical tool. The lenses may be attached to the shaft of the instrument and connected to one another with a housing.

In another embodiment, the detectable feature may include a reflective stripe or stripes. The reflective stripe may be arranged around an outer perimeter of the shaft of the surgical instrument. The reflective stripe may be positioned proximate to the handle of the surgical instrument. The reflective stripe may be formed of a paint containing reflective glass powder.

DESCRIPTION OF THE DRAWINGS

FIG. 8A illustrates a tool assembly including a surgical instrument having a guide stop mechanism in accordance with another embodiment;

FIG. 8B illustrates a tool assembly including a surgical instrument having a guide stop inserted within a modified guide tube in accordance with another embodiment;

DETAILED DESCRIPTION

Figure 1A:
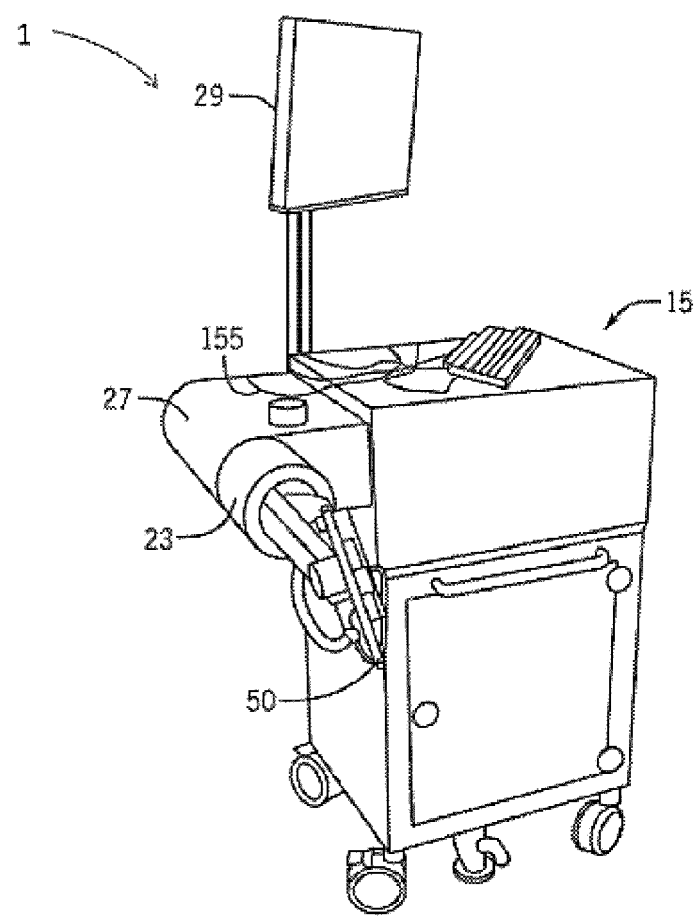
FIGS. 1A-1B illustrate a surgical robot in accordance with one embodiment.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

Figure 1B:
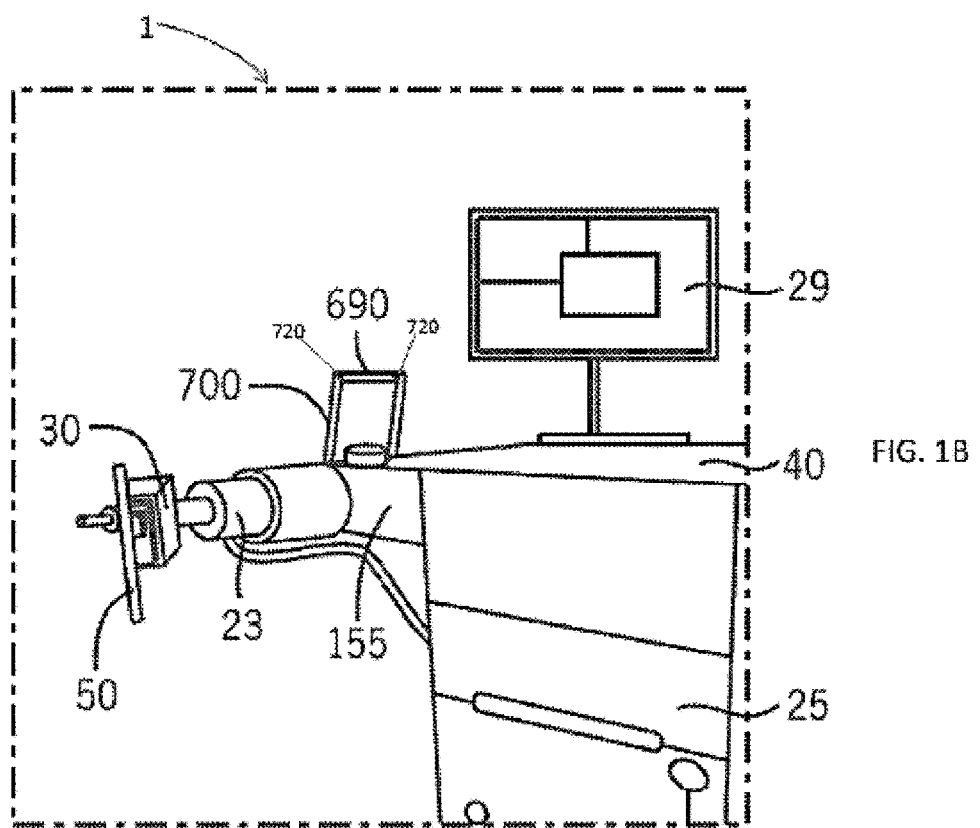
Figure 1C:
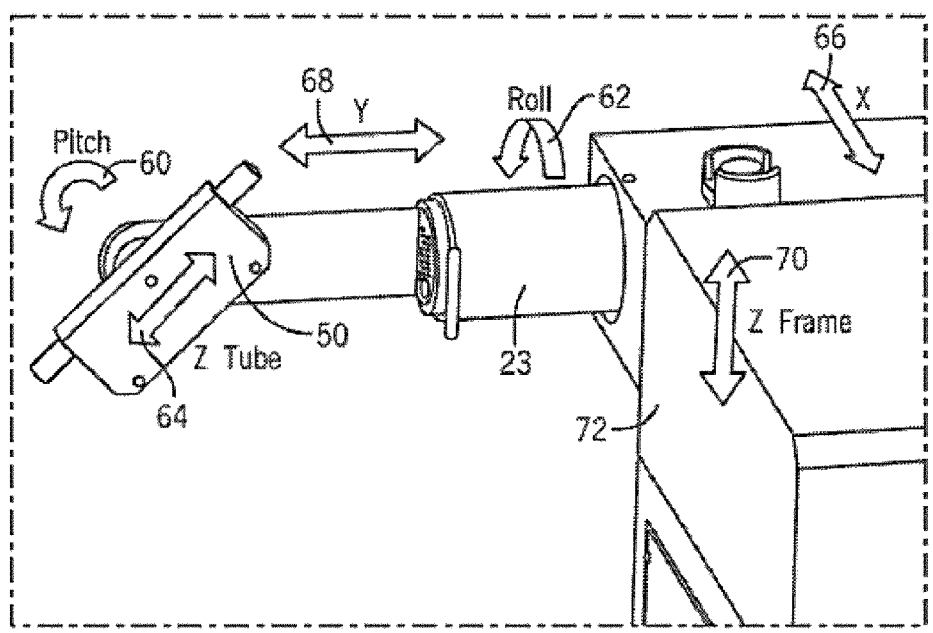
FIG. 1C illustrates a portion of a surgical robot with control of the translation and orientation of the end-effectuator in accordance with another embodiment.

FIGS. 1A-1B illustrate a surgical robot system 1 in accordance with one embodiment of the invention, and FIG. 1C illustrates a portion of a surgical robot system 1 with control of the translation and orientation of the end-effectuator in accordance with another embodiment of the invention. Referring now to FIGS. 1A-1B, some embodiments include a surgical robot system 1. As shown, in some embodiments, the surgical robot 15 can comprise a display 29 and a housing 27. In some embodiments, the display 29 can be attached to the surgical robot 15. In other embodiments, a display 29 can be detached from surgical robot 15, either within a surgical room with the surgical robot 15, or in a remote location. In some embodiments, the housing 27 can comprise a robot arm 23, and an end-effectuator 30 coupled to the robot arm 23 controlled by at least one conventional motor. In some embodiments, the end-effectuator 30 can comprise an instrument used to perform surgery on a patient 18 (such as for example the surgical instrument 35 depicted in FIGS. 3A-3B, 4A-4D, 6A, 7A, 7C, 8A-8B, 9 and 10). In other embodiments, the end-effectuator 30 can be coupled to the surgical instrument 35. In yet other embodiment, the end-effectuator 30 can include a guide tube 50 configured to slidably receive the surgical instrument 35. As used herein, the term "end-effectuator" is used interchangeably with "end-effector" and "effectuator element." In some embodiments, the end-effectuator 30 can comprise any known structure for effecting the movement of the surgical instrument 35 in a desired manner.

FIG. 1C illustrates a portion of a surgical robot 15 with control of the translation and orientation of the end-effectuator in accordance with another embodiment of the invention. As shown, some embodiments include a surgical robot system 1 capable of the utilization of a robot 15 with the ability of moving the end-effectuator 30 along x-, y-, and z-axes (see 66, 68, 70 in FIG. 1C). In this embodiment, the x-axis 66 can be orthogonal to the y-axis 68 and z-axis 70, the y-axis 68 can be orthogonal to the x-axis 66 and z-axis 70, and the z-axis 70 can be orthogonal to the x-axis 66 and the y-axis 68. In some embodiments, the robot 15 can be configured to effect movement of the end-effectuator 30 along one axis independently of the other axes. For example, in some embodiments, the robot 15 can cause the end-effectuator 30 to move a given distance along the x-axis 66 without causing any substantial movement of the end-effectuator 30 along the y-axis 68 or z-axis 70. As used in this context "substantial" means a deviation of less than two degrees from an intended path.

In some further embodiments, the end-effectuator 30 can be configured for selective rotation about one or more of the x-axis 66, y-axis 68, and z-axis 70 (such that one or more of the Cardanic Euler Angles (e.g., roll, pitch, and/or yaw) associated with the end-effectuator 30 can be selectively controlled). In some embodiments, during operation, the end-effectuator 30 and/or surgical instrument 35 can be aligned with a selected orientation axis (labeled "Z Tube" in FIG. 1C) that can be selectively varied and monitored by the robot system 1.

Figure 2:
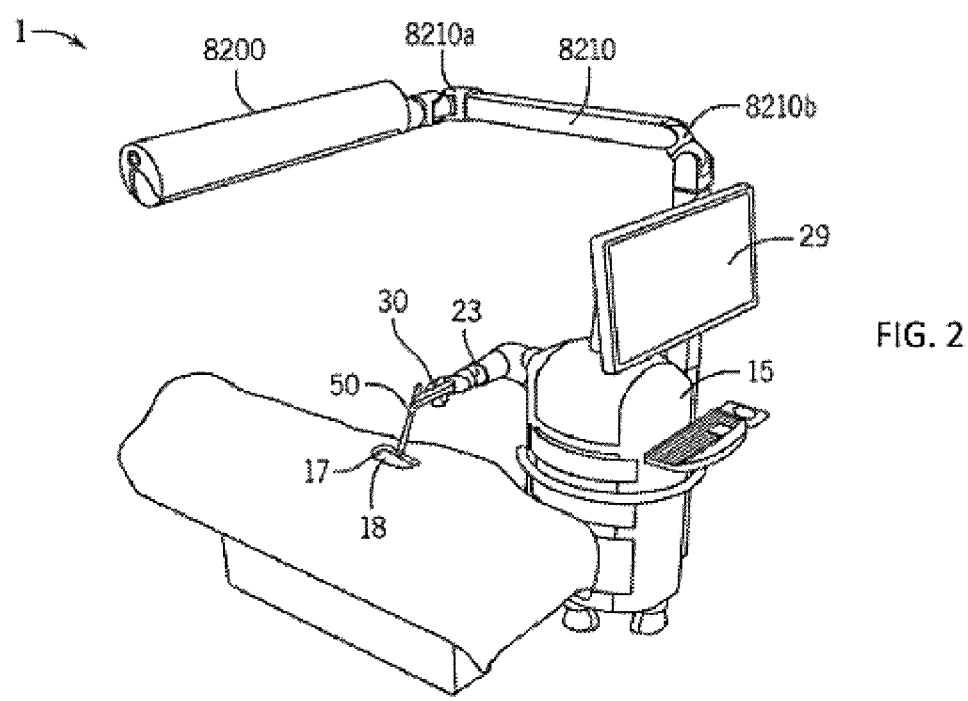
FIG. 2 illustrates a surgical robot operating on a patient in accordance with one embodiment.

In some embodiments, selective control of the translation and orientation of the end-effectuator 30 can permit performance of medical procedures with significantly improved accuracy compared to conventional robots that utilize, for example, a six degree of freedom robot arm 23 comprising only rotational axes. For example, in some embodiments, as shown in FIG. 2, a surgical robot system 1 as depicted in FIGS. 1A-1C, can be used to operate on a patient, and the robot arm 23 that can be positioned above the body of the patient 18, with the end-effectuator 30 selectively angled relative to the z-axis toward the body of the patient 18.

In some embodiments, the position of surgical instrument 35 can be dynamically updated so that surgical robot 15 can be aware of the location of surgical instrument 35 at all times during the procedure. Consequently, in some embodiments, the surgical robot 15 can move the surgical instrument 35 to the desired position quickly, with minimal damage to patient 18, and without any further assistance from a physician (unless the physician so desires). In some further embodiments, the surgical robot 15 can be configured to correct the path of surgical instrument 35 if the surgical instrument 35 strays from the selected, preplanned trajectory. In some embodiments, the surgical robot 15 can be configured to permit stoppage, modification, and/or manual control of the movement of the end-effectuator 30 and/or surgical instrument 35. Thus, in use, in some embodiments, a physician or other user can operate the system 1, and has the option to stop, modify, or manually control the autonomous movement of end-effectuator 30 and/or surgical instrument 35. Further details of the surgical robot system 1 including the control and movement of a surgical instrument 35 by the surgical robot 15 can be found in U.S. patent application Ser. No. 13/924,505, which is incorporated herein by reference in its entirety.

Figures 3A, 3B:
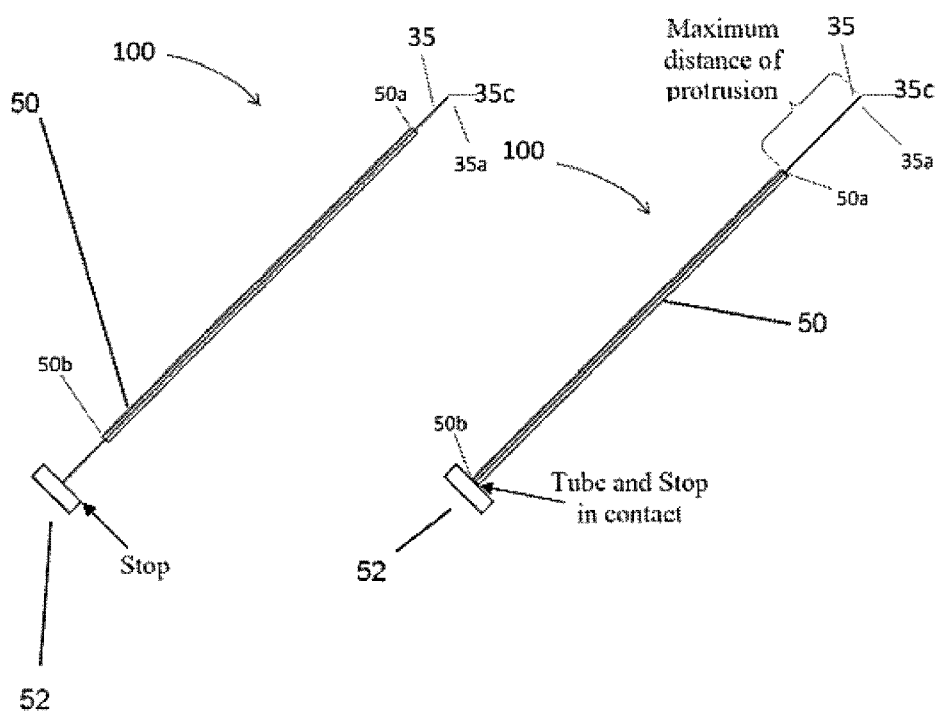
FIGS. 3A-3B each illustrates a tool assembly including a surgical instrument having a guide stop mechanism in accordance with one embodiment.

In some embodiments, a guide tube 50 is used with a surgical instrument 35 to operate on a patient 18. For example, some embodiments include a guide tube 50 comprising a distal end 50a and a proximal end 50b. As used herein, "tube" is used to refer to somewhat hollow structures of any one or more desired cross-sectional shapes. In some embodiments, when the surgical instrument 35 is advanced into the tissue of the patient 18 with the assistance of a guide tube 50, the surgical instrument 35 can comprise a guide stop 52 that is configured to prevent the surgical instrument 35 from advancing when it reaches a predetermined amount of protrusion. For example, FIGS. 3A-3B each illustrates a tool assembly 100 including a surgical instrument 35 having a guide stop 52 in accordance with one embodiment of the invention. The surgical instrument 35 can extend from a proximal end 35b (e.g., handle portion) to a distal end 35a (e.g., tip 35c). As shown in FIG. 3B, when the guide stop 52 contacts the proximal end 50b of the guide tube 50, the instrument 35 is prevented from extending further. In some embodiments, by knowing the lengths of the guide tube 50 and the surgical instrument 35, the distance between the respective ends of the surgical instrument 35, and the location where the guide stop 52 is attached, it is possible to determine the maximum distance past the end of the guide tube 50 that the surgical instrument 35 can protrude (and therefore the length of extension and the location of the tip 35c at the distal end 35a relative to the guide tube distal end 50a during a procedure). In some embodiments, the instrument 35 can be guided by (and at least partially surround) or contact a guide structure.

Figure 4A:
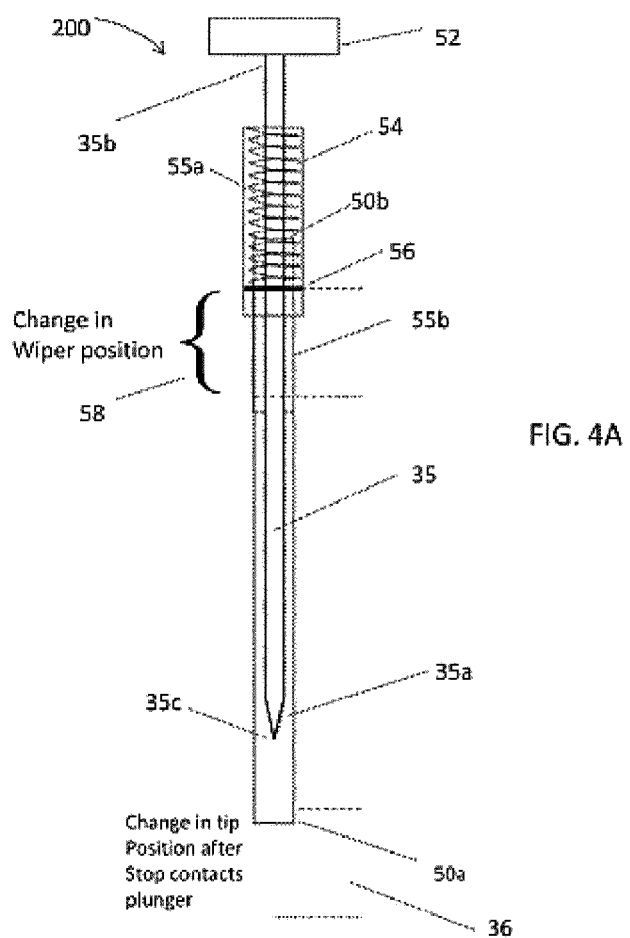
FIGS. 4A-4D each depict a tool assembly including a surgical instrument having a guide stop mechanism in accordance with one embodiment.
Figure 4B:
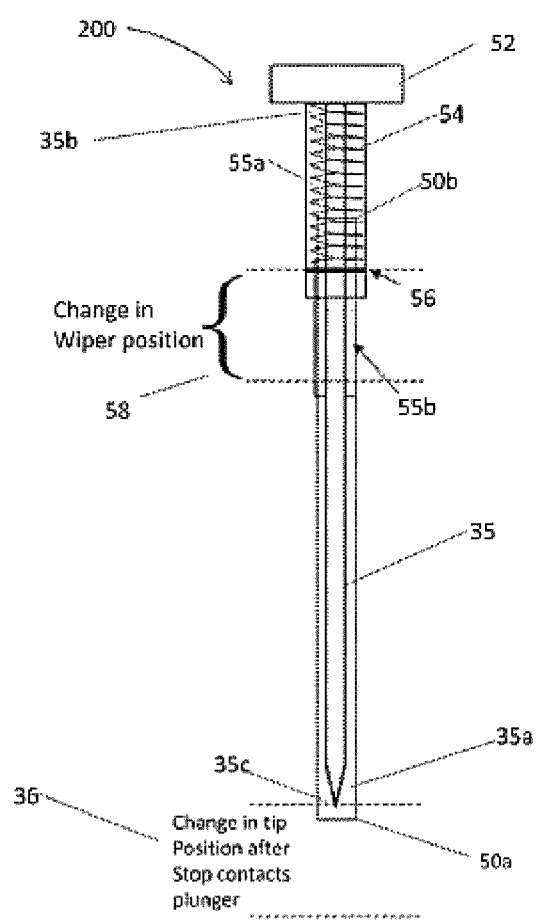
Figure 4C:
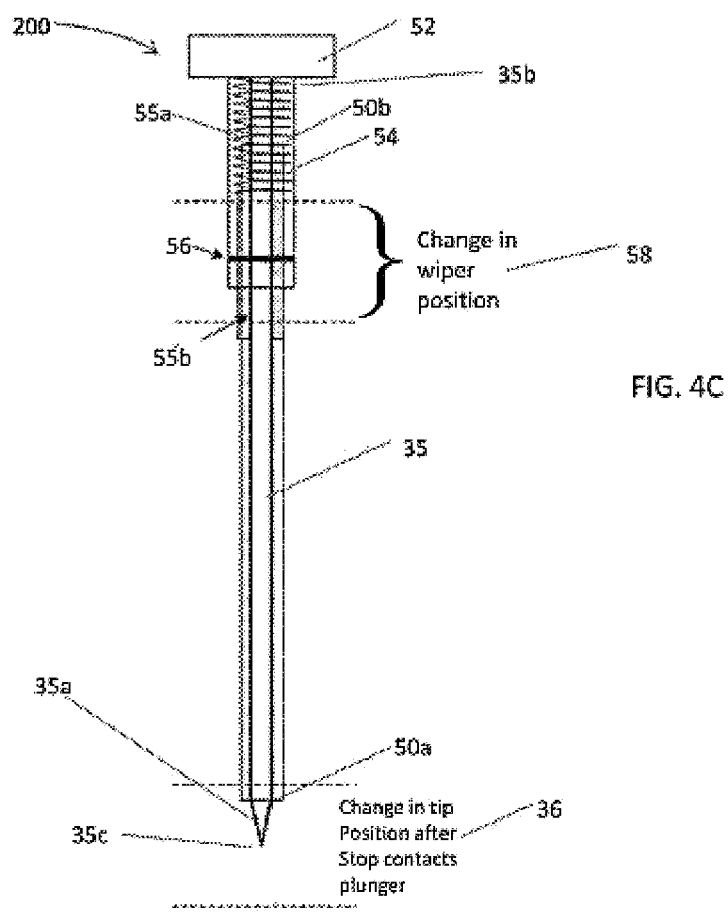
Figure 4D:
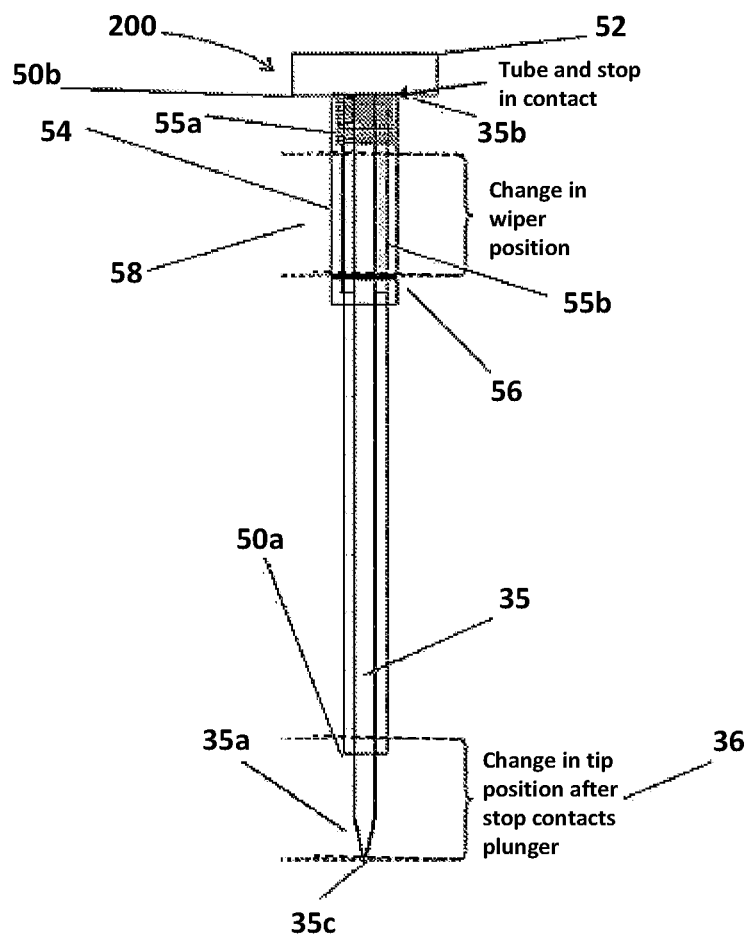

In some embodiments, it can be desirable to monitor not just the maximum protrusion distance of the surgical instrument 35, but also the actual protrusion distance periodically or at any instant during the insertion process. Therefore, in some embodiments, the robot 15 can periodically or substantially continuously monitor the protrusion distance, and in some embodiments, the distance can be displayed (e.g., such as on display 29). In some embodiments, protrusion distance can be substantially continuously monitored using a spring-loaded plunger 54 including a compressible spring-loaded mechanism 55a and sensor pad 55b that has a coupled wiper 56 (see for example FIGS. 4A-4D). In some embodiments, the guide stop 52 on the surgical instrument 35 can be configured to contact the spring-loaded mechanism 55 well before it encounters the proximal end of the guide tube 50. As shown in FIGS. 4A-4D, by comparing the position of the surgical instrument 35 within the guide tube 50, in some embodiments, as the surgical instrument 35 extends toward the distal end 50a of the guide tube 50, the distal end 35a can approach the distal end 50a of the guide tube (FIG. 4B). Further, as the surgical instrument 35 is moved further downwards (i.e., the guide stop 52 moves toward the proximal end 50b of the guide tube 50), the distal end 35a can extend outwards away from the distal end 50a of the guide tube (see FIG. 4C showing the extension of the distal end 35a and change in tip 35c position after the stop 52 contacts the plunger 54, shown as region 36.) Further, as the surgical instrument 35 is moved further downwards and the guide stop 52 contacts the guide tube 50, the distal end 35a can come to a stop, extending away from the distal end 50a of the guide tube 50 (see FIG. 4D, showing the change in tip 35c position (region 36.) As shown in FIGS. 4C-4D, as the guide stop 52 moves toward the proximal end 50b of the guide tube 50, the compressible spring-loaded mechanism 55a within the spring-loaded plunger 54 can compress. One of ordinary skill in the art will recognize that conversely, when the instrument 35 is moved back out of the guide tube 50, as the guide stop 52 moves away from the proximal end 50b of the guide tube 50, the compressible spring-loaded mechanism 55a within the spring-loaded plunger 54 can decompress from the compressed state.

In some embodiments, the tool assembly system 1000 (shown in FIG. 6B) can include a data input/output system including a sensor pad 55b coupled to a wiper 56. As shown, some embodiments include system 1000 comprising at least one processor 1010 coupled to a network interface 1040 including an application interface 1050. In some embodiments, the application interface 1050 is coupled to at least one operating system 1020 and at least one enterprise application 1030. In some embodiments, the at least one processor 1010 can send and receive data from at least the network interface 1040 and the application interface 1050. Further, the network interface 1040 can be coupled to at least one computer readable medium 1060 that in some embodiments can include data sources 1060a and data storage 1060b.

In some embodiments, the surgical robot system 1 may be coupled to the tool assembly system 1000. In some other embodiments, the surgical robot system 1 may comprise the tool assembly system 1000. In some embodiments, the data input/output interface 1100 may be coupled directed to the display 29 (e.g., to directly display from one or more sensors), and in other embodiments, the data input/output interface 1100 may be coupled to the surgical robot system 1 or the display 29, or both. In some embodiments, the data input/output interface 1100 may include a conventional low voltage circuit coupled to one or more sensors 55b, 56, 310, and 510. In other embodiments, the data input/output interface 1100 may be coupled to a conventional low voltage circuit coupled to one or more sensors 55b, 56, 310, and 510. In some embodiments, the one or more sensors 55b, 56, 310, and 510 may be powered by the data input/output interface through a conventional low voltage circuit. In some other embodiments, the one or more sensors 55b, 56, 310, and 510 may be powered through a conventional low voltage circuit and coupled to the data input/output interface.

In some embodiments, the at least one processor 1010 can receive data from at least one data input/output interface 1100. As depicted in FIG. 6B, in some embodiments, the data input/output interface 1100 can include at least the sensor pad 55a and coupled wiper 56. In some embodiments, when the wiper 56 moves across the position sensor pad 55b, its linear position is sampled by the tool assembly system 1000 and may be processed using the at least one processor 1010. For example, in some embodiments, a calculation of the distance by which the surgical instrument 35 protrudes past the distal end 50a of the guide tube 50 may be processed substantially in real-time. For example, as shown in FIGS. 4A-4D, as the position of the surgical instrument 35 within the guide tube 50 is changed, as the surgical instrument 35 extends toward the distal end 50a of the guide tube 50, the wiper 56 can move toward the distal end 50a of the guide tube and across the sensor pad 55b within the wiped region 58 (e.g., see the movement from FIG. 4B to FIG. 4C). Further, as the surgical instrument 35 is moved further downwards toward the distal end 50a of the guide tube 50, and the guide stop 52 contacts the guide tube 50 at the proximal end, the wiper 56 can move toward the distal end 50a of the guide tube 50 and across the sensor pad 55b toward the lower end of the wiped region 58 (see FIG. 4D).

In some embodiments, as the wiper 56 moves across the sensor pad 55b toward the lower end of the wiped region 58, the tool assembly system 1000 can communicate the position of the wiper 56 and/or movement of the wiper 56 with respect to the sensor pad 55b. As described earlier, in some other embodiments, the surgical robot system 1 may comprise the tool assembly system 1000, and the data input/output interface 1100 may be coupled to the surgical robot system 1 to enable the surgical robot system 1 to read the wiper 56 position on the sensor pad 55b, or movement of the wiper 56 with respect to the sensor pad 55b.

Figures 5A, 5B, 5C:
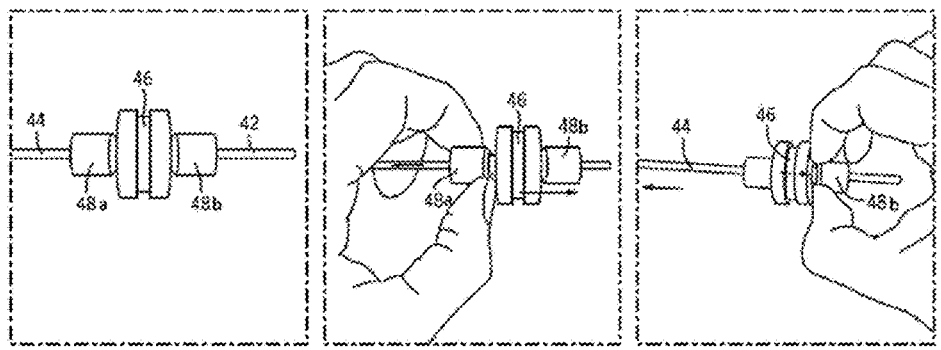
FIGS. 5A-5C each illustrates tools for manually adjusting a drill stop with reference to drill bit markings in accordance with one embodiment.
Figure 5D:
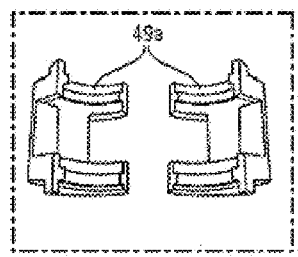
FIGS. 5D-5F each illustrates tools for locking and holding a drill bit in a set position in accordance with one embodiment.
Figure 5E:
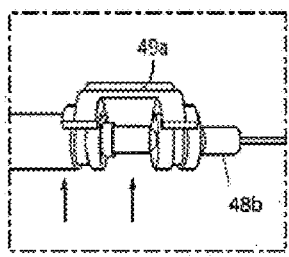
Figure 5F:
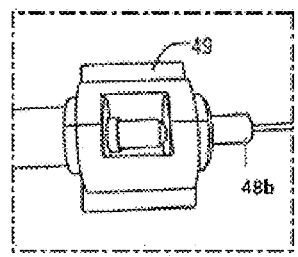
Figure 5G:
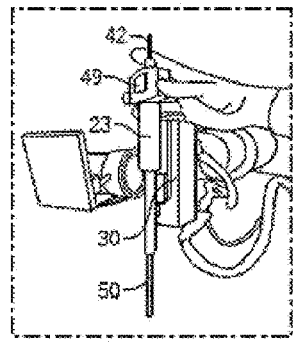
FIGS. 5G-5H each illustrates methods of use of the tools as depicted in FIGS. 5A-5F with a robot end effectuator coupled to a robot system.
Figure 5H:
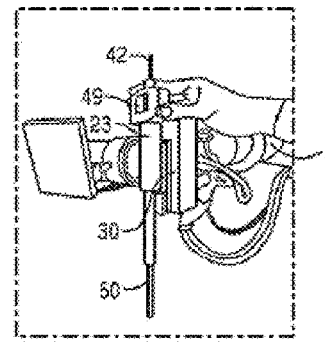

In some embodiments, the surgical instrument can comprise a drill bit 42. Some embodiments include instruments 35 that enable the stop on a drill bit 42 to be manually adjusted with reference to markings 44 on the drill bit 42. For example, FIGS. 5A-5C each illustrate tools for manually adjusting a drill stop 46 with reference to drill bit 42 markings 44 in accordance with one embodiment of the invention. Further, FIGS. 5D-5F each illustrate tools for locking and holding a drill bit in a set position in accordance with one embodiment of the invention, and FIGS. 5G-5H each illustrate methods for use of the tools as depicted in FIGS. 5A-5F with a robot end effectuator 30 coupled to a surgical robot system 1. As shown, in some embodiments, the drill bit 42 can include commercially available oppositely oriented one-way spring-loaded release mechanisms 48a, 48b on each end of the drill stop 46. When not being pulled against their spring, one-way release mechanisms prevent movement in one direction but allow free movement in the opposite direction. For example, in FIG. 5A, the resting release 48a on the left side of the stop 46 allows the drill bit 42 to move freely through the release 48a from right to left but prevents movement of the drill bit 42 from left to right. The release 48b to the right of the stop 46 allows the drill bit 42 to move freely through the release 48b from left to right but prevents movement from right to left. In some embodiments, when neither release 48a, 48b is being pulled it is therefore not possible to move the bit 42 in either direction. In some embodiments, if the release 48a or 48b on one end of the drill stop 46 is pulled, it is possible to move the drill stop 46 up the shaft of the drill bit 42, away from the direction of pull. In some embodiments, if the release 48a or 48b on the other end of the drill stop 46 is pulled, it is possible to move the drill stop 46 down the shaft (away from the direction of pull, see the direction of movement in FIGS. 5B and 5C). The direction in which the release 48a, 48b is pulled is opposite to the direction in which movement of the drill stop 46 is allowed so that accidental pulling of one release 48a, 48b does not result in unintended movement of the drill stop 46. For example, pulling the release 48a toward the left in FIG. 5B allows the drill stop 46 to be moved toward the right. In some embodiments, if neither release mechanism 48a, 48b is pulled, the drill stop 46 will not move in either direction, even if bumped.

Some embodiments include the ability to lock and hold the drill bit 42 in a set position relative to the guide tube 50 in which it is housed. For example, in some embodiments, the drill bit 42 can be locked by locking the drill stop 46 relative to the guide tube 50 using a locking mechanism. FIGS. 5D-5H illustrates tools for locking and holding a drill bit 42 in a set position in accordance with one embodiment of the invention. In some embodiments, the locking mechanism 49 shown in FIG. 5F can comprise two clam shells 49 (shown in FIG. 5D). In some embodiments, a drill bit 42 can be locked into position by assembling the clam shells around the drill stop 46 (shown in FIG. 5E). For example, this feature allows the user to lock the drill bit 42 in a position such that the tip slightly protrudes past the end of the guide tube 50 (see FIGS. 5G and 5H). In this position, the user can force the guide tube 50 to penetrate through soft tissues to force the guide tube 50 to contact bone (for example during a percutaneous spine screw insertion). Further details of the tools illustrated in FIGS. 5A-5G and described above can be found in co-pending U.S. patent application Ser. No. 13/924, 505 from which this application claims priority 35 U.S.C. § 120, and which is incorporated herein by reference in its entirety.

In some embodiments, the tool assembly system 1000 can include the data input/output interface 1100 with at least one position sensor 310. In some embodiments, the at least one processor 1010 can send and receive data from at least the network interface 1040 and the application interface 1050 and may receive data from the data input/output interface 1100 with at least one position sensor 310.

Figure 6A:
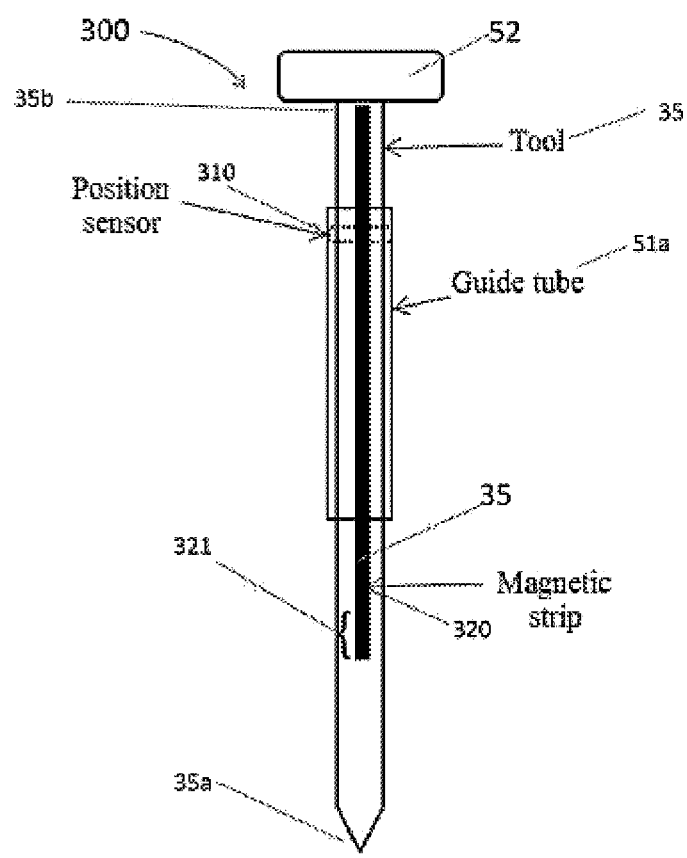
FIG. 6A illustrates a tool assembly including a surgical instrument having a sensor enabled guide stop mechanism in accordance with one embodiment.
Figure 6B:
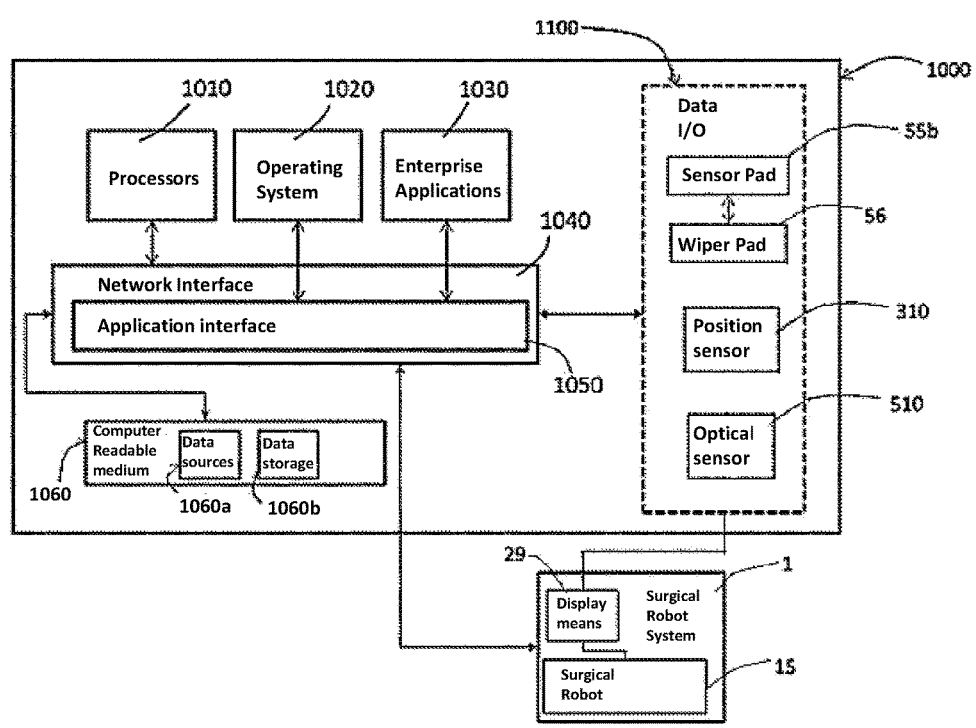
FIG. 6B illustrates a tool assembly system architecture in accordance with one embodiment.

FIG. 6A illustrates a tool assembly 300 including a surgical instrument 35 having a sensor enabled guide stop 52 in accordance with one embodiment of the invention. As shown, in some embodiments, the surgical instrument 35 can include a magnetic strip 320 extending along some portion of the longitudinal length of the instrument 35, and the surgical instrument 35 can include at least one position sensor 310. The embodiment shown in FIG. 6A includes a magnetic strip 320 that extends from a region substantially immediately adjacent to the guide stop 52, and extending to approximately three quarters of the length of the surgical instrument 35.

In some other embodiments, the magnetic strip 320 may extend closer to or farther away from the distal end 35a of the surgical instrument 35. As shown, in some embodiments, the magnetic strip 320 is positioned on the outer surface of the surgical instrument 35. However, in some other embodiments, the magnetic strip 320 can be positioned below the outer surface of the instrument 35 (i.e., the magnetic strip 320 may be embedded in the instrument 35). In some embodiments, the magnetic strip 320 comprises a thickness that is sufficient to retain adequate mechanical integrity. For example, in some embodiments, the magnetic strip 320 comprises a thickness that is sufficient to retain adequate durability during use, while having with enough magnetic field flux to be detected by the position sensor 310.

In some embodiments, the magnetic strip 320 can comprise a thin, flexible, rigid or semi-rigid magnetic material with a thickness of between about 0.001 and about 0.15 inches. In some embodiments, the magnetic strip 320 may be thinner than 0.001 inches, and in other embodiments, the magnetic strip 320 may be thicker than 0.15 inches. In some embodiments, the magnetic strip 320 comprises a self-supporting tape or similar material that can be cut to size and adhered to the surgical instrument 35. In other embodiments, the magnetic strip 320 is formed on the surgical instrument 35 from a liquid or semi-liquid (e.g., magnetic paint that is applied to the surface of the instrument 35 in defined locations which then dries to form the magnetic strip 320). In some embodiments, the magnetic strip 320 comprises a ferrite-based magnetic material. In other embodiments, the magnetic strip 320 comprises a rare-earth based magnetic material (e.g., a neodymium-based permanent magnet). In some further embodiments, the magnetic strip 320 comprises an alnico-based magnetic material (i.e., an aluminum-nickel-cobalt based magnetic material). For example, in some embodiments, the magnetic strip 320 can comprise a thin, flexible, rigid or semi-rigid magnetic strip 320 that comprises a material selected from a group consisting of ferrite-based magnetic material, a neodymium-based permanent magnet, an alnico-based magnetic material, and mixtures thereof. Alternatively, in some other embodiments, the magnetic strip 320 is formed on the surgical instrument 35 from a liquid or semi-liquid (e.g., magnetic paint) that comprises a material selected from a group consisting of ferrite-based magnetic material, a neodymium-based permanent magnet, an alnico-based magnetic material, and mixtures thereof. In some embodiments, the magnetic strip 320 can be embedded within the interior structure of the instrument 35. For example, it may be positioned in the core of the instrument 35. In other embodiments, if the instrument 35 is tubular, the magnetic strip 320 can be placed on the inside surface of the tubular orifice.

In some embodiments, the tool assembly 300 can include the position sensor 310 coupled to the guide tube 51a (see FIG. 6A). In some embodiments, the position sensor 310 can be a Hall-effect sensor capable of varying an output voltage in response to a magnetic field detected from the magnetic strip 320. In some embodiments, the position sensor 310 can comprise a magnetic sense-coil, or magneto-resistive read-head. In some embodiments, as the position sensor 310 moves with respect to the magnetic strip 320, and magnetic fluctuation is detected, an output signal is generated by the data input/output interface 1100. In some embodiments, an insertion of the surgical instrument 35 in the guide tube 51a can be detected using the position sensor 310. In some embodiments, the magnetic strip 320 can include a variable magnetic field flux capable of being detected by the position sensor 310 as it moves with respect to the magnetic strip 320. For example, in some embodiments, the magnetic field flux of the magnetic strip 320 can rise and fall periodically through at least a portion of the longitudinal length of the magnetic strip 320. In the case of the position sensor 310 being a Hall-effect sensor, this movement can produce a varying an output voltage in response to a magnetic field detected from the magnetic strip 320 as it moves from a region of low magnetic field flux to a region of higher magnetic field flux.

In some embodiments, magnetic strip 320 can comprise alternative arrangements of regions of higher and lower magnetic field flux strength capable of being detected by the position sensor 310 as it moves with respect to the magnetic strip 320. In some other embodiments, the alternative arrangements of regions of higher and lower magnetic field flux strength can comprise a magnetic bar code capable of being detected by the magnetic strip 320 and processes using the at least one processor 1010 through the data input/output interface 1100. In some embodiments, the arrangements of regions of higher and lower magnetic field flux strength can comprise a magnetic bar code (depicted as the magnetically coded region 321 of the magnetic strip 320 shown in FIG. 6A). In some embodiments, as least some fraction of the magnetically coded region 321 and can be capable of being detected by the magnetic strip 320 for the purpose of identifying the surgical instrument 35. For example, in some embodiments, a surgical instrument 35 can include a magnetic strip 320 that includes a magnetically coded region 321 with at least a type code of the surgical instrument 35. Moreover, in some embodiments, the surgical robot system 1 can include a safety protocol to perform a check of the surgical instrument 35 prior to its use in a surgical procedure. In some embodiments, an insertion of the surgical instrument 35 in the guide tube 51a for example, can be detected using the position sensor 310 which can be capable of reading the magnetically coded region 321 within the magnetic strip 320 as it passes the sensor 310. In some embodiments, information about the instrument 35 that will be inserted into the guide tube 51a can be stored magnetically and permanently or semi-permanently in the magnetic strip 320 before surgery. Then, during surgery, when the tool is introduced in the guide tube 51a, the sensor 310 can read the magnetically coded region 321 of the strip 320 and detect data regarding the tool's diameter, length, shape, or other important information. These data can be automatically conveyed to the processor 1010 and displayed to the user via data input/output interface 1100.

Figure 7A:
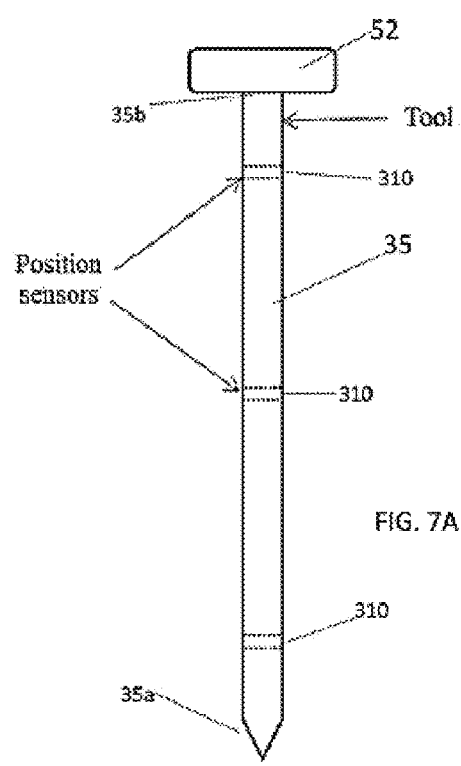
FIG. 7A illustrates a tool comprising a surgical instrument having a guide stop mechanism in accordance with another embodiment.

Some embodiments can include additional or alternative position sensors 310. For example, FIG. 7A illustrates a surgical instrument 35 having a guide stop 52 in accordance with another embodiment of the invention. As shown, the surgical instrument 35 can include three position sensors 310, substantially equally spaced on the surgical instrument 35. In some embodiments, an insertion of the surgical instrument 35 in the guide tube 51a can be detected using the position sensor 310, and the movement of the surgical instrument 35 within a guide tube 51a can be detected as it passes over the remaining position sensors (located approximately half-way down the length of the surgical instrument 35 and adjacent the distal end 35a of the surgical instrument 35). It should be apparent to those of ordinary skill in the art that different lengths of guide tube 51a and instrument 35 can be assembled that necessitate different numbers of position sensors 310 such that the magnetic strip 320 is always adjacent to at least one sensor 310 at any longitudinal position of the instrument 35 within the guide tube 51*a*.

Figure 7B:
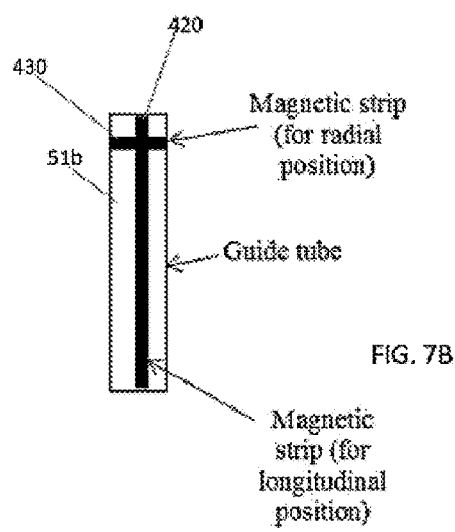
FIG. 7B is a modified guide tube for use with the tool assembly shown in FIG. 7C in accordance with one embodiment.
Figure 7C:
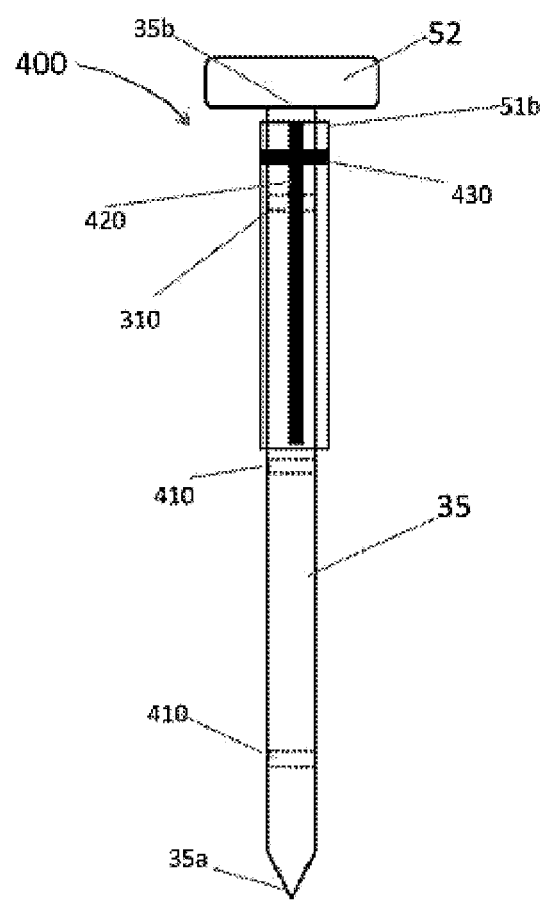
FIG. 7C shows the tool shown in FIG. 7A inserted within the modified guide tube shown in FIG. 7B to form a tool assembly in accordance with one embodiment.

In some other embodiments, the tool assembly 400 (shown in FIG. 7C) can include an alternative guide tube 51*b* including a longitudinal magnetic strip 420 and a radial magnetic strip 430. As used herein, "tube" is intended to cover circular and other shaped structures which may or may not form a complete circle or other enclosing structure. For example, FIG. 7B is a modified guide tube 51*b* for use with the instrument 35 shown in FIG. 7A in accordance with one embodiment of the invention. FIG. 7C shows the tool assembly 400 including the instrument 35 shown in FIG. 7A inserted within the modified guide tube 51*b* shown in FIG. 7B in accordance with one embodiment of the invention. In some embodiments, an insertion of the surgical instrument 35 in the guide tube 51*b* can be detected using the position sensor 310 using the longitudinal magnetic strip 420, and the movement of the surgical instrument 35 within a guide tube 51*b* can be detected as it passes over the remaining position sensors (located approximately half-way down the length of the surgical instrument 35 and adjacent the distal end 35*a* of the surgical instrument 35) using the longitudinal magnetic strip 420. In some embodiments, a rotational movement of the instrument within the guide tube 51*a* can be detected using the radial magnetic strip 430 as it moves with respect to any one of the positions sensors 310. For example, in some embodiments, the tool assembly system 1000 can include the data input/output interface 1100 with at least one position sensor 310. The at least one processor 1010 can send and receive data from at least the network interface 1040 and the application interface 1050, and may receive data from the data input/output interface 1100 with at least one position sensor 310 through an interaction with either the longitudinal magnetic strip 420 or the radial magnetic strip 430. Therefore, in some embodiments, the surgical robot system 1 can detect at least the movement of the surgical instrument 35 longitudinally with respect the guide tube 51*b*, and when the instrument 35 is twisting within the guide tube 51*b*. In some other embodiments, the instrument 35 can be coupled to an exterior surface of a guide tube.

In addition to magnetic field based sensing, some embodiments include optical sensing of the movement of a surgical instrument 35 in a guide tube. For example, FIG. 8A illustrates a surgical instrument 35 having a guide stop 52 in accordance with another embodiment of the invention, and FIG. 8B illustrates a tool assembly 500 including a surgical instrument 35 having a guide stop 52 inserted within a modified guide tube 51*c* in accordance with another embodiment of the invention. As shown, in some embodiments, the surgical instrument 35 can include a plurality of high contrast markings 520 distributed along at least a partial longitudinal length of the instrument 35. In some other embodiments, the plurality of high contrast markings 520 may extend over substantially the entirety of the longitudinal length of the instrument 35.

In some embodiments, the modified guide tube 51*c* can include at least one optical sensor 510 capable of sensing at least one of the plurality of high contrast marking 520. In some embodiments, as the surgical instrument 35 is inserted in the guide tube 51*c*, the at least one optical sensor 510 can be capable of sensing at least one of the plurality of high contrast marking 520. Further, in some embodiments, the tool assembly system 1000 can include the data input/output interface 1100 coupled with at least one of plurality of high contrast marking 520. The at least one processor 1010 can send and receive data from at least the network interface 1040 and the application interface 1050 and may receive data from the data input/output interface 1100 with at least one of the plurality of high contrast marking 520, through an interaction with the at least one optical sensor 510. Therefore, in some embodiments, the surgical robot system 1 can detect at least the movement of the surgical instrument 35 longitudinally with respect the guide tube 51*c* as the optical sensor 510 detects at least one of the plurality of high contrast markings 520.

In some embodiments, the optical sensor 510 can be a photodiode, a phototransistor, a fiber-optic sensor, a photomultiplier, a CCD, a camera or a combination of those described. In some embodiments, the optical sensor 510 can detect ambient light reflected from the surgical instrument 35 including the plurality of high contrast marking 520. In other embodiments, a conventional light source (e.g., an incandescent bulb or an LED light) can be used in combination with the optical sensor 510 and high contrast marking 520, and the optical sensor 510 can detect light emitted by the light source, reflected from the surgical instrument 35 including the plurality of high contrast markings 520.

Figure 1D:
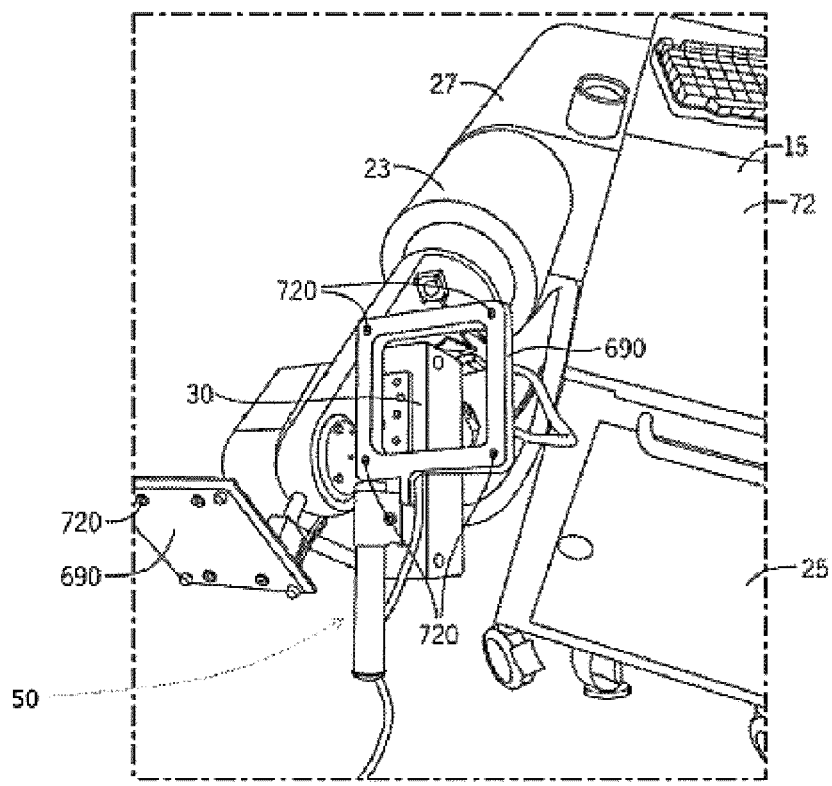
FIG. 1D illustrates a partial view of a surgical robot having a plurality of optical markers mounted for calibration and tracking movement in accordance with one embodiment.
Figure 9:
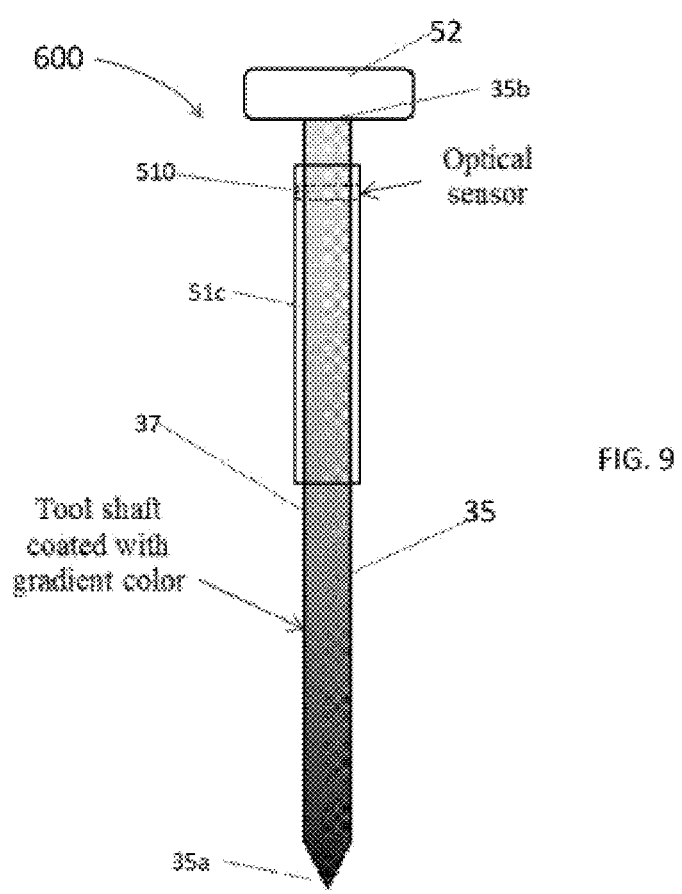
FIG. 9 illustrates a tool assembly including a surgical instrument having a guide stop inserted within a modified guide tube in accordance with another embodiment.

Some embodiments can include an alternative optical recognition of a surgical instrument 35. For example, FIG. 9 illustrates a tool assembly 600 including a surgical instrument 35 having a guide stop 52 inserted within a modified guide tube 51*c* in accordance with another embodiment of the invention. As shown, in some embodiments, the surgical instrument 35 can include an optically graduated coating 37. In some embodiments, the optically graduated coating 37 can include a graduation of color across at least a partial longitudinal length of the instrument 35. In some other embodiments, the optically graduated coating 37 can include a graduation in light reflectivity across at least a partial longitudinal length of the instrument 35. For example, in some embodiments, the optically graduated coating 37 can include a graduation in light reflectivity extending from the proximal end (shown as a substantially colorless region adjacent the guide stop 52 in FIG. 9) to a darker region adjacent the distal end 35*a*. In some embodiments, as the surgical instrument 35 is inserted in the guide tube 51*c*, the at least one optical sensor 510 can be capable of sensing the coating 37. Further, in some embodiments, the tool assembly system 1000 can include the data input/output interface 1100 coupled with the coating 37. The at least one processor 1010 can send and receive data from at least the network interface 1040 and the application interface 1050, and may receive data from the data input/output interface 1100 with at least one of the plurality of high contrast marking 520, through an interaction with the at least one optical sensor 510. Therefore, in some embodiments, the surgical robot system 1 can detect at least the movement of the surgical instrument 35 longitudinally with respect the guide tube 51*c* as the optical sensor 510 detects the coating 37. For example, when the surgical instrument 35 is initially inserted into the guide tube 51*c*, the optical sensor 510 may detect a low level of light due to the coating 37 comprising a dark color and/or a low reflectivity. As the surgical instrument 35 is further inserted into the guide tube 51*c*, the optical sensor 510 may detect an increasing level of light due to the optical sensor 510 moving over a coating 37 comprising a gradually increasingly lighter color and/or a higher reflectivity In some embodiments, the robotic surgical system 1 can comprise a plurality of tracking markers 720 configured to track the movement of the robot arm 23, the end-effectuator 30, and/or the surgical instrument 35 in three dimensions. It should be appreciated that three dimensional positional information from tracking markers 720 can be used in conjunction with the one dimensional linear positional information from absolute or relative conventional linear encoders on each axis of the robot 15 to maintain a high degree of accuracy. In some embodiments, the plurality of tracking markers 720 can be mounted (or otherwise secured) thereon an outer surface of the robot 15, such as, for example and without limitation, on the base 25 of the robot 15, or the robot arm 23 (see for example FIG. 1B). In some embodiments, the plurality of tracking markers 720 can be configured to track the movement of the robot 15 arm, the end-effectuator 30, and/or the surgical instrument 35. In some embodiments, the robotic surgical system 1 can utilize the tracking information to calculate the orientation and coordinates of the surgical instrument 35 based on encoder counts along the x-axis 66, y-axis 68, z-axis 70, the Z-tube axis 64, and the roll 62 and pitch 60 axes. Further, in some embodiments, the plurality of tracking markers 720 can be positioned on the base 25 of the robot 15 spaced from the surgical field 17 to reduce the likelihood of being obscured by the surgeon, surgical tools, or other parts of the robot 15. In some embodiments, at least one tracking marker 720 of the plurality of tracking markers 720 can be mounted or otherwise secured to the end-effectuator 30 (see for example FIG. 1D). Further embodiments, at least one optical marker of the plurality of optical tracking markers 720 can be positioned on the robot 15 between the base 25 of the robot 15 and the end-effectuator 30 instead of, or in addition to, the markers 720 on the base 25 of the robot 15. In some embodiments, the positioning of one or more tracking markers 720 on the end-effectuator 30 can maximize the accuracy of the positional measurements by serving to check or verify the end-effectuator 30 position (calculated from the positional information from the markers on the base 25 of the robot 15 and the encoder counts of the z 70, x 66, y 68, roll 62, pitch 60, and Z-tube 64 axes). In some embodiments, the at least one tracking marker 720 can be mounted to a portion of the robot 15 that effects movement of the end-effectuator 30 and/or surgical instrument 35 along the x-axis to enable the tracking marker 720 to move along the x-axis 66 as the end-effectuator 30 and surgical instrument 35 move along the x-axis 66 (see FIG. 1D). In some embodiments, the placement of the tracking markers 720 as described can reduce the likelihood of a surgeon blocking the tracking marker 720 from the cameras or detection device, or the tracking marker 720 becoming an obstruction to surgery.

In certain embodiments, because of the high accuracy in calculating the orientation and position of the end-effectuator 30 based on the tracking marker 720 outputs and/or encoder counts from each axis, it can be possible to very accurately determine the position of the end-effectuator 30. For example, in some embodiments, without requiring knowledge of the counts of axis encoders for the z-axis 70 (which is between the x-axis 66 and the base 25), knowing only the position of the markers 720 on the x-axis 66 and the counts of encoders on the y axis 68, roll axis 62, pitch 60, and Z-tube axes 64 can enable computation of the position of the end-effectuator 30. In some embodiments, the placement of markers 720 on any intermediate axis of the robot 15 can permit the exact position of the end-effectuator 30 to be calculated based on location of such markers 720 and counts of encoders on axes (66, 62, 60, 64) between the markers 720 and the end-effectuator 30. Further details of the surgical robot system 1 including the control, movement and tracking of the surgical robot 15 and of a surgical instrument 35 can be found in U.S. patent application Ser. No. 13/924,505, which is incorporated herein by reference in its entirety.

Some embodiments include one or more markers 725 coupled to the surgical instrument 35. In some embodiments, the markers 720, 725 can comprise conventional light-emitting diodes or an Optotrak® diode or reflective Polaris sphere capable of being tracked using a commercially available infrared optical tracking system such as Optotrak®. Optotrak® is a registered trademark of Northern Digital Inc., Waterloo, Ontario, Canada. In some embodiments, light emitted from and/or reflected by the markers 720, 725 can be read by cameras 8200 used to monitor the location and movement of the robot 15 (see for example the camera 8200 mounted on the camera arm 8210 and capable of movement through camera arm joint 8210a and camera arm joint 8210b shown in FIG. 2). In some other embodiments, the markers 720, 725 can comprise a radio-frequency and/or electromagnetic reflector or transceiver and the camera 8200 can include or be replaced by a radio-frequency and/or electromagnetic transceiver.

Figure 10:
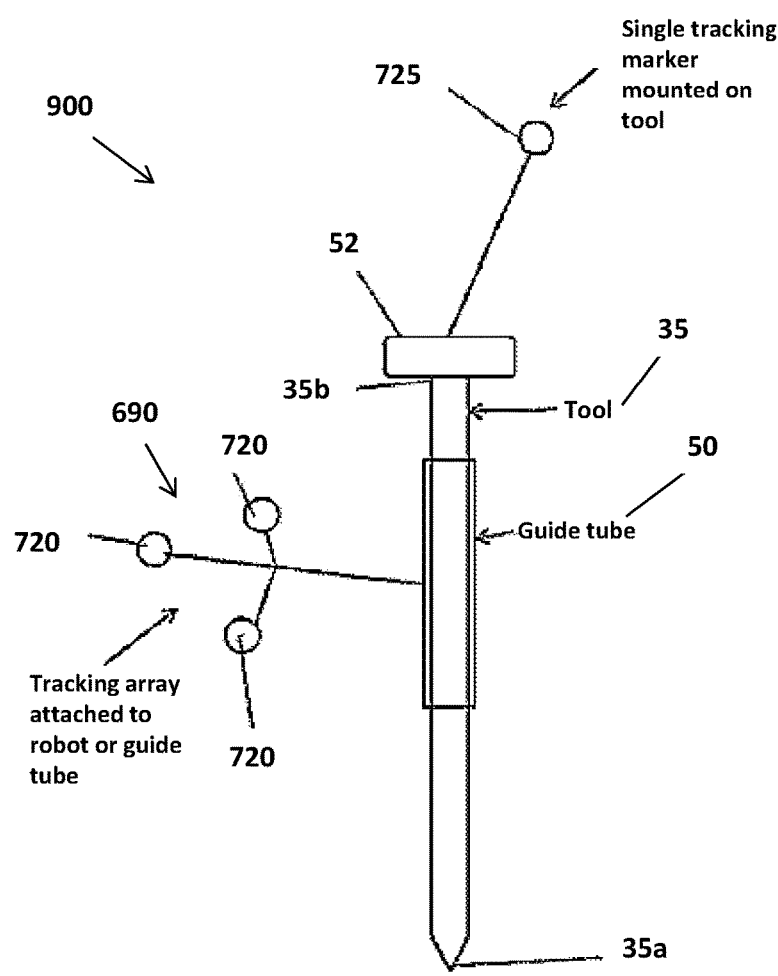
FIG. 10 illustrates a tool assembly including a surgical instrument having at least one tracking marker in accordance with a further embodiment.
Figure 11:
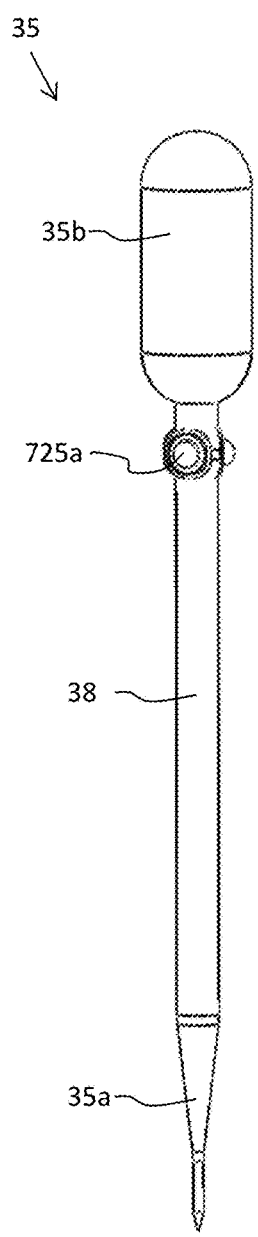
FIG. 11 is a surgical instrument using reflective lenses as one or more tracking markers according to another embodiment.

FIG. 10 illustrates a tool assembly 900 including a surgical instrument 35 having at least one tracking marker 725 in accordance with a further embodiment of the invention. In some embodiments, a single marker 725 can be adequate to determine the linear position of the instrument 35 within the guide tube 50 if the guide tube 50 is tracked with a tracking array 690. As depicted in FIG. 10, if this single tracking marker 725 is coupled to the tool is offset from the longitudinal midline of the tool 50, the marker's position in space relative to the guide tube 50 can provide information about both the radial orientation and longitudinal position of the instrument 35 within the guide tube 50. In some other embodiments, a plurality of markers 725 can be used to determine the linear position of the instrument 35 within the guide tube 50 if the guide tube 50 is tracked with a tracking array 690.

In this embodiment, a single marker 725 extends from the tool 35 to track depth, and the distance away from the tool 35 can also be used as an identifier of which tool 35 is currently in the guide tube 50 of the end effector 30. Depending on the system, it may be possible that a single marker 725 may not be readily seen when the surgeon's hand is in the way or if it rotates around out of view. Thus, it is contemplated that two, three, or more markers 725 could be used instead of a single marker 725. Even if multiple markers are used, there is a chance that the markers 725 may overlap each other and the system may fail to distinguish them as individual markers 725. Accordingly, in some embodiments, it may be useful to have one or more markers 725 which extend around at least a portion of or the entire perimeter or circumference of the outer surface of the tool 35.

Turning now to FIGS. 11, 12, and 13A-13C, alternative versions of the one or more markers 725 coupled to the surgical instrument 35 are shown. In these embodiments, the markers 725 extend around at least a portion of the outer surface of the tool 35 such that the markers 725 should be visible regardless of the rotation or orientation of the tool 35. In FIGS. 11 and 13A-13C, the marker 725 includes one or more reflective lenses 725a, and in FIG. 12, the marker 725 includes one or more reflective stripes 725b, for example, applied directly to the surface of the surgical instrument 35. These markers 725a, 725b may be reflective in that they are capable of reflecting light from another source. For example, markers 725a, 725b may reflect or bounce back infrared light from an infrared source positioned at some distance away from the markers 725a, 725b.

FIGS. 11 and 13A-13C depict incorporation of one or more reflective lenses 725a on the shaft 38 of the instrument 35 proximate to the proximal end 35b (e.g., near the handle portion or at the handle portion) of the instrument 35. In this embodiment, three reflective lenses 725a are used around the outer surface of the shaft 38 of the instrument 35. Although three lenses 725a are exemplified, it is possible that more or less lenses 725a may be used. It is also possible that more lenses 725a or other markers may be provided at other locations on or extending from the instrument 35. The reflective lenses 725a may form a partial sphere or semi-sphere, and may have a radius of curvature 726 terminating in a substantially flat collar or flange 728. Although not visible, the lenses 725a have a mirrored backing to provide the reflective properties. According to one embodiment, the lenses 725a may include Radix™ lenses, which are reflective tracking markers offered by Northern Digital, Inc. Radix™ is a trademark of Northern Digital Inc., Waterloo, Ontario, Canada. These Radix™ lenses are configured such that they have a housing and backing with a mirror lining the concave surface. These types of lenses are also described in U.S. Patent App. No. 2007/0183041, which is hereby incorporated by reference in its entirety for all purposes.

The lenses 725a may be attached to the instrument 35 or other suitable object to be tracked using any suitable means. For example, the reflective lenses 725a may be attached to the shaft 38 and connected to one another with a housing 40. The housing 40 may protrude from the surface of the shaft 38 and encase at least a portion of the lenses 725a. The housing 40 may be radiused such that it extends from a first portion of the shaft 38 to a second portion of the shaft 38. The housing 40 may also be tapered or curved around the outer portion of each lens 725a (for example, around the outer perimeter of the flange 728 of the lens 725a.

In the embodiment shown, the lenses 725a can be configured such that a plurality of markers 725a (e.g., three markers 725a) are embedded in or near the handle of the tool 35 such that it is not possible for two markers 725a to overlap each other and be mistakenly identified by the system as a single marker. Therefore, as the surgeon rotates the tool 35, such as when advancing a screw, at least one lens 725a is always facing toward the cameras and depth can therefore be tracked.

Figure 12:
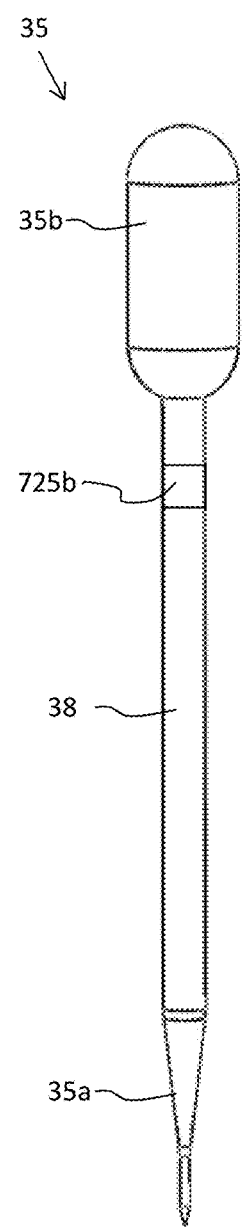
FIG. 12 is a surgical instrument having one or more stripes of reflective material as a tracking marker according to yet another embodiment.
Figure 13A:
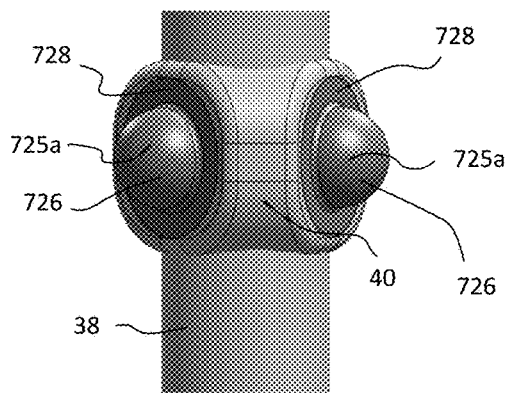
FIGS. 13A-13C depict views of reflective lenses which may be used as tracking markers, for example, with the embodiment shown in FIG. 11.
Figure 13B:
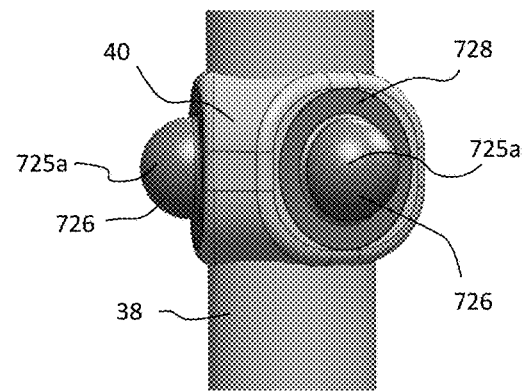
Figure 13C:
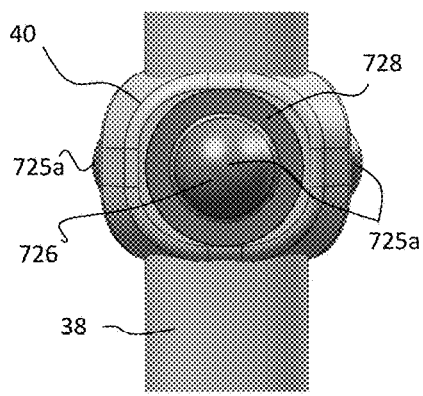

Turning now to FIG. 12, an alternative version of the tracking marker is shown in the form of one or more reflective stripes 725b, for example, applied directly to the surface of the surgical instrument 35. The reflective stripes 725b may be painted on the shaft 38 of the instrument 35 proximate to the proximal end 35b (e.g., near the handle portion or at the handle portion) of the instrument 35. In this embodiment, a single reflective stripe 725b is used around the outer surface of the shaft 38 of the instrument 35. Although one stripe 725b is exemplified, it is possible that more stripes 725b or different shapes or configurations may be used. It is also possible that more stripes 725b or other markers may be provided at other locations on or extending from the instrument 35.

In one embodiment, the reflective stripe 725b is applied using a reflective highway paint to paint the stripe around the shaft 38 of the tool 35. The tracking system then recognizes this stripe 725b, when viewed from any perspective, as being an individual tracked marker and can detect its position. The tool 35 has the stripe 725b painted around the shaft 35 with reflective glass powder adhered to the paint. When photographed, for example, with a flash, the stripe 725b lights up with more reflectivity than the adjacent shaft 38. The stripe 725b can be continuously tracked in 3D by the tracking system as an individual stray marker. Since it is not spherical, one may not expect the stripe 725b to be tracked with high precision. However, the accuracy may be adequate for tracking the depth of the tool 35 within the guide tube 50, especially since it is known that the tool 35 is centered in the guide tube 50 and adjustments to the perceived stripe 725b can be made based on this known centering and the known angle of the guide tube 50.

One or more stripes 725b can be painted, with the benefit of additional stripes being that tools 35 can be distinguished from one another based on the distance between stripes 725b. An advantage of the stripe 725b instead of a spherical tracked marker, for example, is that the stripe 725b has zero profile and should therefore not get in the way of the surgeon's line of sight or disallow insertion of that portion of the shaft 38 into the guide tube 50.

Although several embodiments of the invention have been disclosed in the foregoing specification, it is understood that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

What is claimed is:
1. A medical robot system, comprising:
a robot coupled to an end-effector, the robot configured for controlled movement and positioning of the end-effector, the end-effector including a guide tube;
a motor assembly coupled to the robot, the motor assembly being configured to move the end-effector along one or more of an x-axis, a y-axis, and a z-axis;
a surgical instrument positionable within the guide tube, the surgical instrument including at least one detectable feature; and
a detection device configured and arranged to detect the at least one detectable feature,
wherein a depth of the surgical instrument in the guide tube is determined by the at least one detectable feature,
wherein the at least one detectable feature comprises a plurality of reflective lens, wherein the plurality of reflective lens form a semi-sphere, and have a radius of curvature terminating at a substantially flat collar or flange, wherein the plurality of reflective lens comprises three reflective lenses arranged around an outer perimeter of a shaft of the surgical instrument.

2. The medical robot system of claim 1, wherein the plurality of reflective lens is embedded in a handle of the surgical tool.

3. The medical robot system of claim 1, wherein the plurality of reflective lens includes at least two reflective lenses, and the at least two reflective lenses are attached to the shaft and connected to one another with a housing.

4. The medical robot system of claim 1, wherein the at least one detectable feature comprises at least one reflective stripe.

5. The medical robot system of claim 4, wherein the at least one reflective stripe is arranged around an outer perimeter of a shaft of the surgical instrument.

6. The medical robot system of claim 4, wherein the at least one reflective stripe is positioned proximate to a handle of the surgical instrument.

7. The medical robot system of claim 4, wherein the at least one reflective stripe is formed of a paint containing reflective glass powder.

8. A medical robot system, comprising:
a robot coupled to an end-effector, the robot configured for controlled movement and positioning of the end-effector, the end-effector including a guide tube;
a motor assembly coupled to the robot, the motor assembly being configured to move the end-effector along one or more of an x-axis, a y-axis, and a z-axis;
a surgical instrument positionable within the guide tube, the surgical instrument including at least one detectable feature; and
a detection device configured and arranged to detect the at least one detectable feature,
wherein a depth of the surgical instrument in the guide tube is determined by the at least one detectable feature,
wherein the at least one detectable feature is an optically graduated coating that includes a graduation in light reflectivity extending from a proximal end of the surgical instrument to a darker region adjacent the distal end of the surgical instrument, wherein the plurality of reflective lens comprises three reflective lenses arranged around an outer perimeter of a shaft of the surgical instrument.

* * * * *